(12) United States Patent
Poschalko et al.

(10) Patent No.: US 7,988,953 B2
(45) Date of Patent: Aug. 2, 2011

(54) UV ABSORBING CHROMOPHORES COVALENTLY BONDED TO HYPERBRANCHED POLYMERS

(75) Inventors: Alexander Poschalko, Birsfelden (CH); Ulrich Huber, Erlenbach (CH); Volker Schehlmann, Schopfheim (DE)

(73) Assignee: DSM IP Assets B.V., Heerlen (NL)

( * ) Notice: Subject to any disclaimer, the term of this patent is extended or adjusted under 35 U.S.C. 154(b) by 862 days.

(21) Appl. No.: 10/593,486

(22) PCT Filed: Mar. 23, 2005

(86) PCT No.: PCT/EP2005/003117
§ 371 (c)(1),
(2), (4) Date: Oct. 17, 2006

(87) PCT Pub. No.: WO2005/092282
PCT Pub. Date: Oct. 6, 2005

(65) Prior Publication Data
US 2008/0081025 A1    Apr. 3, 2008

(30) Foreign Application Priority Data
Mar. 25, 2004 (EP) .................................. 04007201

(51) Int. Cl.
*A61K 8/72* (2006.01)
*A61K 8/85* (2006.01)
*A61K 8/86* (2006.01)
*A61Q 17/04* (2006.01)

(52) U.S. Cl. .......... 424/60; 528/405; 528/417; 528/421; 528/486; 528/291; 424/59

(58) Field of Classification Search ................. 424/70.9, 424/60; 528/403, 419, 417, 421
See application file for complete search history.

(56) References Cited

U.S. PATENT DOCUMENTS

| | | | |
|---|---|---|---|
| 5,089,250 A | 2/1992 | Forestier et al. | |
| 5,403,944 A | 4/1995 | Frater et al. | |
| 5,618,520 A | 4/1997 | Hansenne et al. | |
| 5,663,247 A | 9/1997 | Sorensen et al. | |
| 6,037,444 A | 3/2000 | Rannard et al. | |
| 6,114,489 A | 9/2000 | Vicari et al. | |
| 6,143,850 A * | 11/2000 | Keller et al. | 526/304 |
| 6,287,552 B1 * | 9/2001 | Tournilhac et al. | 424/78.03 |
| 6,497,959 B1 | 12/2002 | Mhetar | |
| 6,617,418 B1 * | 9/2003 | Magnusson et al. | 528/417 |
| 6,743,889 B1 | 6/2004 | Tan et al. | |

(Continued)

FOREIGN PATENT DOCUMENTS

EP    1 277 770    1/2003

(Continued)

OTHER PUBLICATIONS

Muscat, Dirk et al, Hyperbranched Polyesteramides—New Dendritic Polymers; Topics in Current Chemistry, vol. 212; Springer-Verlag Berlin Heidelberg 2001; pp. 41-80.*

(Continued)

*Primary Examiner* — Randy Gulakowski
*Assistant Examiner* — Rachel Kahn
(74) *Attorney, Agent, or Firm* — Nixon & Vanderhye P.C.

(57) ABSTRACT

The invention provides a conjugate comprising a hyperbranched polymer covalently bonded to at least three UV absorbing chromophores having an UV absorption maximum $\lambda_{max} \geq 270$ nm.

Figure 1:
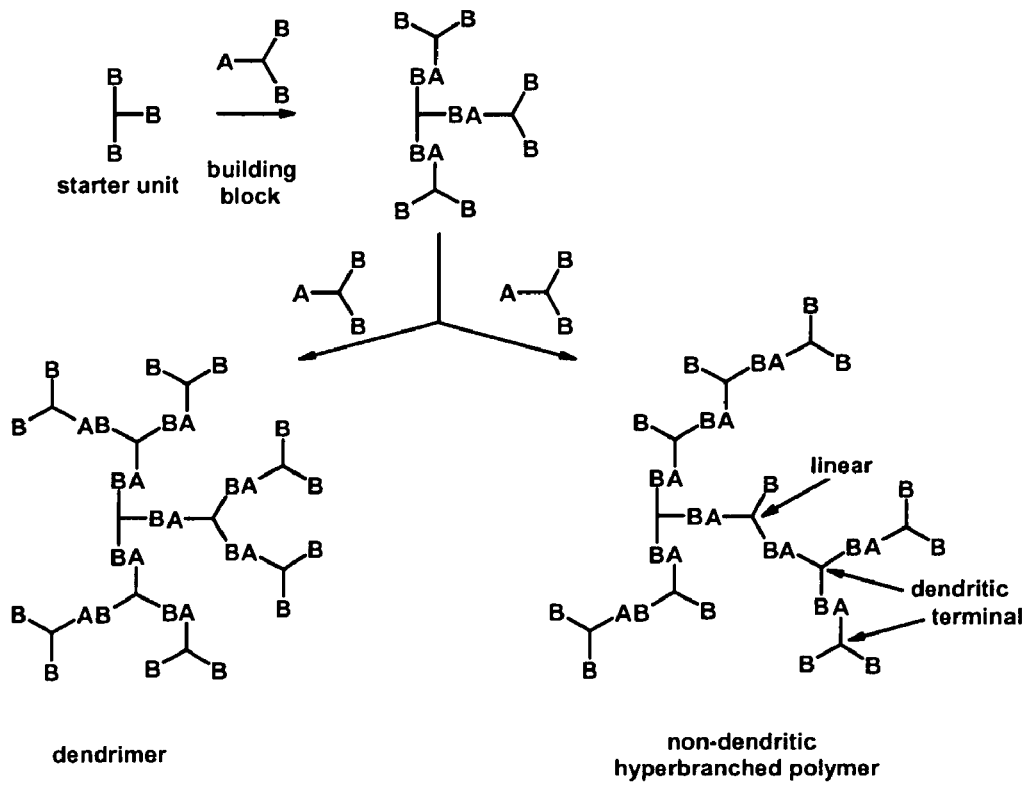

The conjugate is an effective and safe sunscreen which can advantageously be used in cosmetic compositions.

11 Claims, 3 Drawing Sheets

U.S. PATENT DOCUMENTS

| | | | |
|---|---|---|---|
| 6,765,082 B2* | 7/2004 | Sunder et al. | 528/409 |
| 7,507,785 B2* | 3/2009 | Vanmaele et al. | 528/408 |
| 2005/0038167 A1* | 2/2005 | Plummer et al. | 524/445 |

FOREIGN PATENT DOCUMENTS

| | | |
|---|---|---|
| FR | 2 757 389 | 6/1998 |
| WO | WO 93/04665 | 3/1993 |
| WO | WO 97/12882 | 4/1997 |
| WO | WO 02/077074 | 10/2002 |
| WO | WO 02/092668 | 11/2002 |
| WO | WO 03/037830 | 5/2003 |
| WO | 2004/031264 A1 | 4/2004 |

OTHER PUBLICATIONS

Sunder et al; Controlled Synthesis of Hyperbranched Polyglycerols by Ring Opening Multibranching Polymerization; Macromolecules, 1999, 32, 4240-4246.*

Boltorn Dendritic Polymers, Product data summary. On the web at http://www.perstorp.com/upload/boltorn.pdf.*

Sunder et al, Hyperbranched Polyether-Polyols Based on Polyglycerol: Polarity Design by Block Copolymerization with Propylene Oxide; Macromolecules 2000, 33, pp. 309-314.*

Sunder et al, Copolymers of Glycidol and Glycidyl Ethers: Design of Branched Polyether Polyols by Combination of Latent Cyclic AB2 and ABR Monomers; Macromolecules, 2000, 33, 7682-7692.*

Haag et al, An approach to Glycerol Dendrimers and Pseudo-Dendritic Polyglycerols, J Am Chem Soc, 2000, 122, 2954-2955.*

Majoral et al, Dendrimers Containing Heteroatoms (Si, P, B, Ge, or Bi), Chemical Reviews, American Chemical Society, Easton, US, vol. 99, 1999, pp. 845-880.

Zeng et al, "Dendrimers in Supramolecular Chemistry: From Molecular Recognition to Self-Assembly", Chemical Reviews, American Chemical Society, Easton, US, vol. 97, No. 5, 1997, pp. 1681-1712.

Turk et al, "Dendritic Polyglycerol Sulfates as New Heparin Analogues and Potent Inhibitors of the Complement System", Bioconjugate Chem., vol. 15, Jun. 12, 2003, pp. 162-167.

International Search Report mailed Jul. 12, 2005 in PCT/EP2005/003117.

Written Opinion mailed Jul. 12, 2005 in PCT/EP2005/003117.

* cited by examiner building block AB$_2$ monomer C$_2$

UV ABSORBING CHROMOPHORES COVALENTLY BONDED TO HYPERBRANCHED POLYMERS

The present invention relates to conjugates comprising hyperbranched polymers covalently bonded to UV absorbing chromophores, to their preparation and their use. Said conjugates are particularly useful as UV sunscreens, i.e. in compositions for the protection of the human skin and/or hair against harmful effects of sunlight.

There is a constantly increasing need for sunscreen protection agents in a population which is exposed to an increasing amount of damaging sunlight. Repetitive sun exposure can result in skin changes known as photoaged skin. The clinical changes that are seen in photoaged skin differ from those of normally aged skin in the sites of the body protected against sunlight. Among damaging results of extensive sun exposure of the skin there is increased wrinkling, elastosis, pigmentary changes, precancerous and cancerous skin lesions.

Many sunscreen chemicals have been developed in the past protecting against the harmful effect of UV-A (320 nm to 400 nm) and/or UV-B (290 nm to 320 nm) wavelength and even shorter wavelength (UV-C). These chemicals are usually incorporated either alone or in combination with each other into cosmetic or pharmaceutical preparations which are widely known and used.

A good UV absorbing chromophore should have excellent photostability, toxicological and dermatological acceptability, excellent heat stability, very good solubility in cosmetic solvents, in particular in oil or water, compatibility with cosmetic bases, pH stability in the range of 4 to 9, processability into cosmetic formulations, compatibility with other ingredients of cosmetic formulations and with the packaging materials, no staining of textiles, it should be free of color and of neutral or pleasant odor, and it should be free of tackiness and have a low volatility.

Most UV absorbing chromophores used in sunscreen compositions are monomeric compounds, and thus there is the inherent risk that such compounds penetrate the skin barrier, which is highly undesirable.

UV filters on the basis of polysiloxanes which may be either linear or cyclic are described e.g. in WO 93/04665, WO 94/06404, EP-A 538 431, EP-A 392 883 and EP-A 358 584. EP-A 660 701 discloses a photostable, filtering cosmetic composition for protecting human epidermis and hair against UV rays comprising, in a cosmetically acceptable carrier having at least one fatty phase, 0.5 to 4 wt.-% of 4-(tert-butyl) 4'-methoxy dibenzoylmethane and 0.1 to 20 wt.-% of a filtering polymer of a specific benzotriazole silicone type. EP-A 601 080 discloses a filtering cosmetic composition containing, in a cosmetically acceptable carrier, at least one synthetic or natural liposoluble hydrocarbonated polymer bearing at least one UV absorbing group and at least one organopolysiloxane bearing at least one UV absorbing group, the weight ratio between the hydrocarbonated filter polymer and the filter organopolysiloxane being comprised between 0.1 and 5.

With these polysiloxanes the risk of skin penetration is lower, but it is sometimes difficult to incorporate the polysiloxanes in sunscreen compositions due to incompatibility problems which differ depending on the UV absorbing chromophores which are covalently bonded to the polysiloxanes.

In polymeric UV sunscreens the number of UV absorbing chromophores per polymer molecule is usually low. Increasing the number of covalently bonded chromophores often does not result in a higher sun protection factor (SPF).

Therefore, there is a demand for sunscreens which meet the above requirements and which, in particular, have a reduced risk of penetrating the skin. The sunscreens should have comparably, preferably better properties than the sunscreens of the prior art, in particular they should combine a high SPF with a low risk of skin penetration.

It has been surprisingly found that this technical problem can be solved by the subject matter of the present claims, i.e. by a conjugate comprising a hyperbranched polymer covalently bonded to at least three UV absorbing chromophores having an UV absorption maximum $\lambda_{max} \geq 270$ nm.

Compositions comprising UV filters and hyperbranched polymers are known from the prior art. FR-A 2 757 389 discloses a cosmetic filtering composition, comprising a cosmetically acceptable carrier containing at least one UV absorbing agent and at least one polymer selected from the group consisting of hyperbranched polymers and dendrimers. However, the UV absorbing agent is not covalently bonded to the hyperbranched polymer or the dendrimer.

Hyperbranched polymers are known from the prior art. Dendrimers constitute a distinct subtype of hyperbranched polymers (e.g. Sunder et al., Chem. Eur. J. 2000, 6, 2499-2506, where dendrimers are considered as perfectly branched hyperbranched polymers), but further types of hyperbranched polymers have also been reported. For the purpose of the present specification hyperbranched polymers can be divided into dendrimers and non-dendritic hyperbranched polymers.

Dendrimers are hyperbranched polymers that are known per se, having a well-defined chemical structure. In general, dendrimers comprise a core, a defined number of generations of branches, or spindles, and terminal groups. The generations of spindles comprise structural units, which are identical for the same generation of spindles and which can be identical or different for different generations of spindles. The generations of spindles extend radially in a geometrical progression from the core. The terminal groups of a dendrimer of the Nth generation are the terminal functional groups of the spindles of the $N^{th}$ generation or terminal generation. Such polymers are described e.g. in G. R. Newkome, C. N. Moorefield, F. Vögtle, Dendritic Molecules, VCH Verlagsgesellschaft, 1996, the disclosures of which being incorporated by reference herein.

Non-dendritic hyperbranched polymers are molecular constructions having a branched structure, generally around a core. In contrast to the highly symmetric structure of dendrimers, the structure of most non-dendritic hyperbranched polymers lacks symmetry: the base units or building blocks used in the construction of the non-dendritic hyperbranched polymer can be of different natures and they are distributed irregularly. The branches of the polymer can be of different natures and lengths. The number of building blocks can be different depending on the different branching.

Hyperbranched polymers may be synthesized e.g. by polycondensation or polyaddition of one or more building block, such as $AB_m$, wherein A and B are complementary functional groups capable of reacting with one another, m being an integer $\geq 2$, but other preparation processes can be envisaged.

For the purpose of the present specification a "building block" is preferably defined as a compound having at least three independent functional groups which may be involved in a polymerization reaction. Thus, a building block according to the present specification is a branched monomer. The term "building block" encompasses compounds having more than one kind of functional groups, such as $AB_m$ wherein $m \geq 2$, and compounds having only a single kind of functional group, such as $C_q$ wherein $q \geq 3$. Preferably, a building block has 50 atoms or less.

Suitable functional groups A or B may be e.g. $CO_2H$, OH, $NH_2$, HC≡C, $H_2C$=CH, epoxydes, azirines, —SH, —CN, —COCl, anhydrides, lactones, lactames, isocyanates, thioisocyanates, carbonates, carbamates, etc. In case of a radical polymerization, however, an ethylenically unsaturated group comprises two "functional groups" in the above meaning.

Hyperbranched polymers are strictly to be distinguished from conventional branched, grafted or cross-linked polymers or resins. The term "hyperbranched polymer" is widely used in the literature to define a distinct class of compounds (cf. e.g. M. K. Mishra and S. Kobayashi, Star and Hyperbranched Polymers, Marcel Dekker, 2000; Sunder et al., Chem. Eur. J. 2000, 6, 2499-2506; U.S. Pat. No. 6,399,048). Preferably, by every addition step of a building block to the polymeric backbone the overall number of branches contained in the polymeric backbone is increased by at least one further branch. Said new branch contains (or consists of) a reactive group which itself may be involved in subsequent polymerization steps thereby extending the length of its branch(es) and generating new branches. In theory, the number of branches increases exponentially. In perfect dendritic structures, every reactive group of a new branch subsequently reacts with further building blocks thereby extending the existing branches and generating new branches simultaneously; only the building blocks of the outermost generation do not react with further building blocks. In non-dendritic hyperbranched polymers, however, some of the "new branches" are not involved in further polymerization steps but remain in the free reactive forms of their functional groups. In this regard it can also be referred to e.g. A. Sunder et al., Chem. Eur. J. 2000, 6, No. 14, 2499-2506.

In the simplest case, a hyperbranched polymer is preferably composed of n identical building blocks $AB_m$, m being an integer $\geq 2$ and A and B being complementary functional groups, i.e. functional groups A are capable of reacting with functional groups B but not with functional groups A, and functional groups B are capable of reacting with functional groups A but not with functional groups B. Such a hyperbranched polymer may be written as $(AB_m)_n$. The polymerization reaction may be initiated by one of the n building blocks $AB_m$ or, alternatively, by a starter unit $B_k$ wherein $k \geq 1$. Such a hyperbranched polymer may be written as $(B_k)(AB_m)_n$. For example, in FIG. 1 the initial reaction steps in the polymerization of e.g. building blocks $AB_2$ with the optional starter unit $B_3$ have been illustrated.

Figure 2:
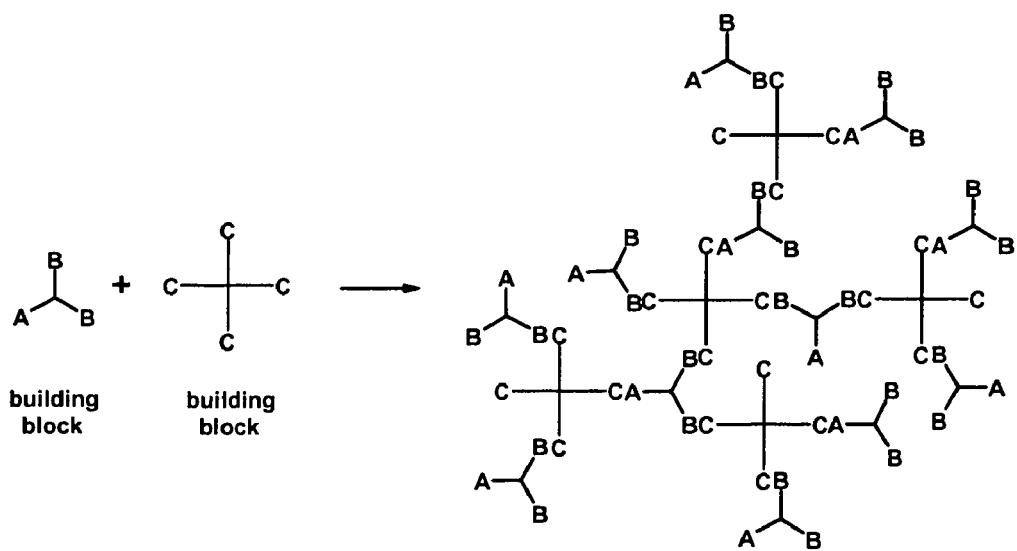

However, hyperbranched polymers may also be composed of more than one type of building block. For example, in FIG. 2 a hyperbranched polymer is depicted which is composed of n building blocks $AB_2$ and r building blocks $C_4$, wherein functional groups A are capable of reacting with functional groups C, but neither with functional groups A nor B. Furthermore, functional groups B are also capable of reacting with functional groups C, but neither with functional groups A nor B. Finally, functional groups C are not capable of reacting with one another. In consequence, the building blocks $AB_2$ may not react directly with one another; therefore, monomers $C_4$ are needed as "bridges" between functional groups A and A, A and B, and B and B. Such a hyperbranched polymer may be written as $(AB_2)_n(C_4)_r$. Since building block $AB_2$ as well as building block $C_4$ contains more than two functional groups, every addition of each building block results in an increase of the number of branches—every addition of building block $AB_2$ generates one further branch and every addition of building block $C_4$ generates 2 further branches (cf. FIG. 2).

Figure 3:
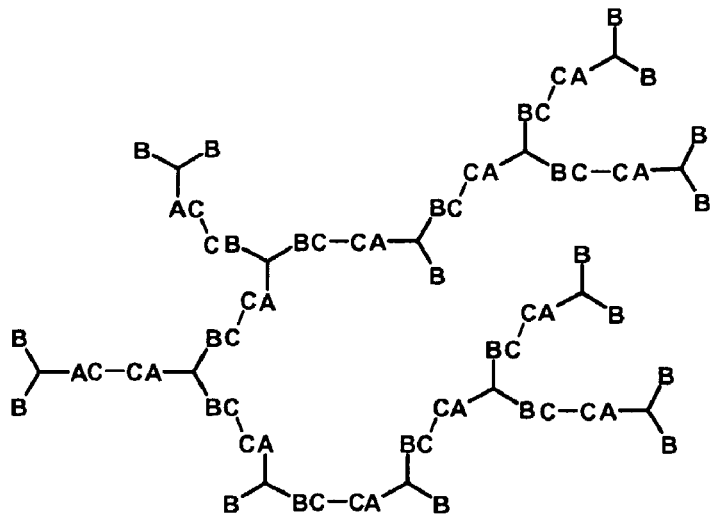
Figure 3:
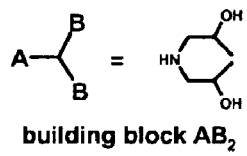
Figure 3:
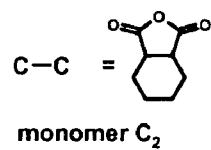
Figure 3:
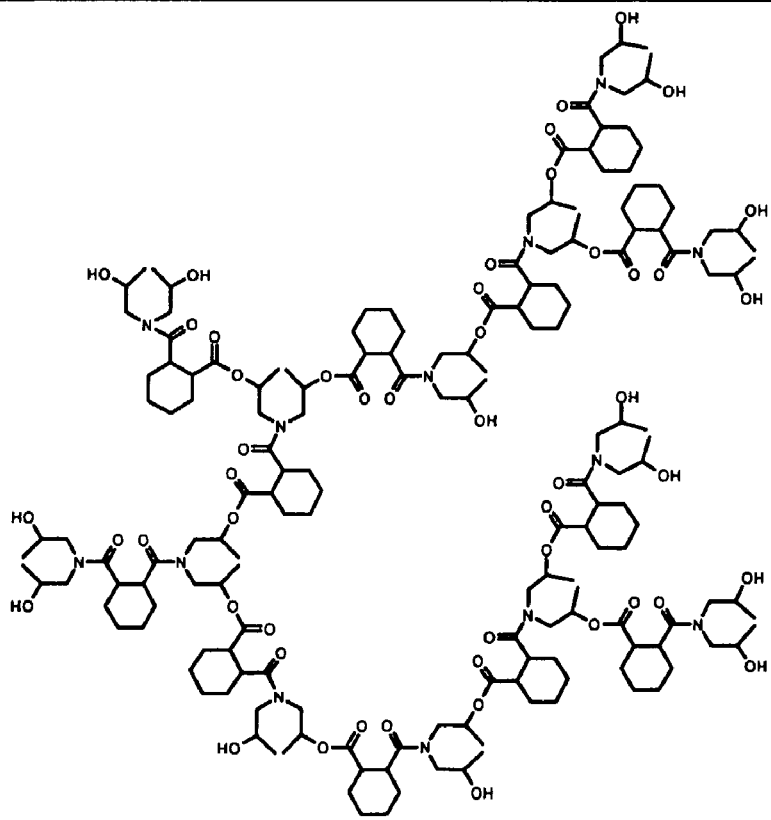

Furthermore, hyperbranched polymers may also be composed of e.g. one type of building block in combination with a bifunctional monomer. For example, the above system comprising building blocks $AB_2$ and building blocks $C_4$ may be modified in that the number of functional groups of building block $C_4$ is reduced from 4 to 2. As $C_2$ contains two functional groups only, $C_2$ may not be regarded as "building block" according to the above definition; its addition to the polymeric backbone does not generate a new branch per se. However, the addition of $C_2$ is required to enable the addition of further building blocks $AB_m$ to the growing polymer finally resulting in an increase of the number of branches. Therefore, the polymerization product depicted in FIG. 3 also constitutes a hyperbranched polymer. To distinguish compounds not generating further branches per se from building blocks, for the purpose of the present invention compounds such as $C_2$ may be denoted as "monomers". Such a hyperbranched polymer may be written as $(AB_m)_n(C_2)_r$. It is an essential feature of such a system in which a building block is polymerized in the presence of a monomer that the functional groups of the monomer are not capable of reacting with one another. Therefore, every monomer may only be covalently bonded to building blocks and hence, no polymer branches are possible which are exclusively composed of monomers.

Hyperbranched polymers may be classified according to their degree of branching (DB). While linear polymers constitute an extreme exhibiting a DB of 0%, dendrimers constitute the other extreme possessing a DB of 100%. Hyperbranched polymers, however, are characterized in that 0<DB$\leq$100%. Thus, the general structure of hyperbranched polymers encompasses dendritic structures as a specific substructure. The DB describes the relative perfection of a hyperbranched structure compared with the perfect structure, i.e. the dendrimer. Thus, dendrimers are said to be "perfect" hyperbranched polymers (cf. e.g. U.S. Pat. No. 6,399,048).

In the following the DB will be defined for polymers derived from a single kind of building block $AB_m$ wherein m=2, i.e. $AB_2$. However, the same principle is also applicable to further hyperbranched polymers, such as hyperbranched polymers composed of building blocks $AB_m$ in which m>2 and hyperbranched polymers composed of more than one kind of building block, respectively.

Non-dendritic hyperbranched polymers derived from building blocks of the $AB_2$-type and exhibiting a DB between 0 and 100% are characterized in that they contain three different kinds of building blocks (cf. FIG. 1):
building blocks in which both functional groups B are covalently bonded to functional groups A of two further building blocks (dendritic),
building blocks in which only one functional group B is covalently bonded to a functional group A of another building block (linear), and
building blocks in which neither functional group B is covalently bonded to a functional group A of another building block (terminal).

In contrast, in the structure of an idealized dendrimer composed of building blocks $AB_2$ both functional groups B within any preceding spindle (except the outermost spindle) are covalently bonded to functional groups A of the building blocks $AB_2$ within the next spindle. Thus, an ideal dendrimer contains only two different kinds of building blocks, namely dendritic and terminal building blocks, but no linear building blocks (cf. FIG. 1).

For the purpose of the present specification a "dendritic building block" is preferably defined as a building block in which all of its polymerizable functional groups are involved in the polymerization reaction. In contrast, a "terminal building block" is preferably defined as a building block in which only one of its polymerizable functional groups is involved in the polymerization reaction.

When the hyperbranched polymer is derived from building blocks of the $AB_2$-type, the DB may be calculated according to the following formula:

$$DB = \frac{2D}{2D+L} \cdot 100\%,$$

wherein D and L represent the fraction of dendritic and linear building blocks (cf. D. Hölter et al., Acta Polym. 1997, 48, 30). Usually, by the known synthetic methods, the DB of hyperbranched polymers ranges from 15 to 90%. In an ideal random polymerization of $AB_2$ building blocks, the ratio of dendritic, linear and terminal building blocks, which can be determined e.g. by NMR (cf. Sunder et al., Macromolecules 1999, 32, 4240-4246), is expected to be 1:2:1 corresponding to a DB of 50%. However, steric factors and reactivity differences often lead to values between 50 and 67%. A further increase of DB towards 100% can be achieved by the use of peculiar building blocks exhibiting a strong preference towards the formation of fully branched dendritic building blocks. DBs lower than 50% can be realized e.g. by copolymerization of a building block $AB_2$ with a linear monomer AB. For further details it is referred to e.g. A. Sunder et al., Chem. Eur. J. 2000, 6, No. 14, 2499-2506 and the references cited therein.

For the purpose of the present specification the term "hyperbranched polymer" is preferably defined as a polymer composed of
- at least one type of building block $AB_m$ having complementary functional groups A and B, i.e. functional group A is capable of reacting with functional group B but not with functional group A and functional group B is capable of reacting with functional group A but not with functional group B; or
- at least one type of building block $AB_m$ having non-complementary functional groups, i.e. functional groups which may not directly react with one another but which may be covalently bonded through at least one type of building block $C_q$ (index $q \geq 3$, preferably 3 or 4) and/or through at least one type of monomer $C_2$ having functional groups C which are complementary to functional groups A and B; i.e. functional group A is capable of reacting with functional group C but neither with functional group A nor B, functional group B is capable of reacting with functional group C but neither with functional group A nor B, and functional group C is capable of reacting with functional groups A and B but not with functional group C.

Thus, the term "hyperbranched polymers" comprises e.g. dendrimers (DB=100%) as well as non-dendritic hyperbranched polymers (DB<100%), such as dendrimers having defects in their branched structure or an incomplete degree of branching, asymmetrically branched dendrimers, starburst polymers, multi-arm star polymers, highly branched polymers and the corresponding copolymers (cf. e.g. M. K. Mishra and S. Kobayashi, Star and Hyperbranched Polymers, Marcel Dekker, 2000). The hyperbranched structure results in characteristic properties that strongly depend on the degree of branching: (i) a globular, relatively compact shape, and (ii) absence of entanglements.

The hyperbranched polymers according to the invention preferably exhibit an average degree of branching (DB) $\geq 15\%$, preferably $\leq 25\%$, more preferably $\geq 30\%$, most preferably $\geq 40\%$, in particular $\geq 50\%$. In a preferred embodiment of the present invention the average degree of branching is within the range of $15\% \leq DB \leq 90\%$, more preferably $25\% \leq DB \leq 85\%$, most preferably $40 \leq DB \leq 80\%$, in particular $45\% \leq DB \leq 75\%$. In another preferred embodiment of the present invention the average degree of branching is $\geq 75\%$, preferably $\geq 80\%$, more preferably $\geq 85\%$, most preferably $\geq 90\%$, in particular $\geq 95\%$.

Preferably, the hyperbranched polymer has an average molecular weight $M_w$ within the range of from 500 to 50,000 g mol$^{-1}$, more preferably 750 to 25,000 g mol$^{-1}$, most preferably 1,000 to 10,000 g mol$^{-1}$.

Preferably, the hyperbranched polymer comprises an average number of 2 to 600 dendritic building blocks, more preferably 2 to 250, most preferably 3 to 100, in particular 4 to 25.

Preferably, the hyperbranched polymer comprises an average number of 2 to 100 terminal building blocks, more preferably 2 to 50, most preferably 3 to 30, in particular 4 to 25.

In a preferred embodiment of the present invention the hyperbranched polymer has a glass transition temperature $T_g \leq 150°$ C., preferably $T_g \leq 100°$ C., more preferably $T_g \leq 70°$ C. In a preferred embodiment of the present invention the glass transition temperature of the hyperbranched polymer is within the range of from 60° C. to 100° C., preferably from 30° C. to 70° C., more preferably from 10° C. to 40° C. (measured by DSC).

The hyperbranched polymers according to the invention are preferably based on polyester, polyamide, polyesteramide, polyether, polythioether, polyether ketone, polyalkylene imine, polyamidoamine, polyether amide, polyarylene, polyalkane, polyalkylene aromatic compounds, polyarylacetylene and or polymers containing phosphorous or silicone, or combinations thereof.

Particularly preferred hyperbranched polymers are the hyperbranched polyesteramides disclosed in EP-A 1 306 401, the hyperbranched polymers commercialized by DSM N.V. under the trademark HYBRANE, and the hyperbranched polymers disclosed in Sunder et al., Macromolecules 1999, 32, 4240-4246 and ibid. 2000, 33, 309-320.

In a preferred embodiment of the present invention the hyperbranched polymer is covalently bonded to at least two, more preferably to at least three, most preferably to at least four, in particular to at least five UV absorbing chromophores. When more than one UV absorbing chromophore is present in the conjugate, the UV absorbing chromophores may be of a different or of the same type. Preferably, all UV absorbing chromophores are identical.

UV absorbing chromophores which can be used according to the present invention are preferably chromophores which are known sunscreens.

It is a characteristic feature of such UV absorbing chromophores according to the present invention that they have an UV absorption maximum $\lambda_{max} \geq 270$ nm. Usually, the UV portion of the electromagnetic spectrum is defined to range from about 10 nm to about 400 nm. Many UV absorbing chromophores have more than one (local, relative) absorption maximum within said range. For example, the anion $C_6H_5O^-$ exhibits a strong UV absorption maximum at 235 nm having a molar extinction coefficient $\epsilon$ of 9,400 M$^{-1}$cm$^{-1}$ and another weaker UV absorption maximum at 287 nm having a molar extinction coefficient E of 2,600 M$^{-1}$cm$^{-1}$. For the purpose of the present specification only the UV absorption maximum within the range of 270 nm$\leq \lambda_{max} \leq 400$ nm is relevant, even if there are further and even stronger UV absorption maxima at $\lambda_{max} < 270$ nm. When there is more than one local UV absorption maximum within the range of 270 nm≦$\lambda_{max}$≦400 nm only the strongest maximum (highest molar extinction coefficient) is relevant.

Preferably, the UV absorption maximum $\lambda_{max}$ of the UV absorbing chromophore is ≧275 nm, more preferably ≧280 nm, most preferably ≧285 nm, in particular ≧290 nm. In a preferred embodiment of the present invention the UV absorption is in the UV-B range and the UV absorption maximum $\lambda_{max}$ of the UV absorbing chromophore is e.g. within the range of from 290 nm to 320 nm. In another preferred embodiment of the present invention the UV absorption is in the UV-A range and the UV absorption maximum $\zeta_{max}$ of the UV absorbing chromophore is e.g. within the range of from 320 nm to 400 nm. Preferably, the UV absorbing chromophore is colorless, i.e. it does not significantly absorb irradiation at wavelengths >400 nm.

Preferably, at its UV absorption maximum $\lambda_{max}$≧270 nm the UV absorbing chromophore exhibits a molar extinction coefficient ε≧250, preferably ≧400, more preferably ≧600, most preferably ≧750, in particular ≧1,000 [$M^{-1}$ $cm^{-1}$].

Preferably, the conjugate according to the present invention comprises a structure represented by general formula (I)

$\{[Q](Y^1)_g\}(LX)_p(Y^2)_h$      (I), wherein
  $Y^1$ and $Y^2$ independently represent UV absorbing chromophores;
  $\{[Q](Y^1)_g\}$ represents the hyperbranched polymer, covalently bonded to g UV absorbing chromophores $Y^1$;
  $(LX)_p$ represents p linker units LX, wherein independently the distal end of each linker unit LX bears a functional group X either being
    covalently bonded to an UV absorbing chromophore $Y^2$, or
    covalently bonded to a capping group, or
    in its free reactive form, and wherein the proximal end of each linker unit LX is covalently bonded to the hyperbranched polymer; and
  wherein
    index g is an integer, wherein 0≦g≦100, preferably 0≦g≦80, more preferably 0≦g≦60, still more preferably 1≦g≦40, most preferably 0≦g≦25, in particular g=0;
    index h is an integer, wherein 0≦h≦p; and
    index p is an integer, wherein 0≦p≦100, preferably 0≦p≦80, more preferably 0≦p≦60, most preferably 1≦p≦40, in particular 3≦p≦25;
    with the proviso that g+h≧3.

The conjugate according to the present invention contains at least three UV absorbing chromophores $Y^1$ or $Y^2$ which are covalently bonded to the hyperbranched polymer. Such an UV absorbing chromophore may be bonded to the hyperbranched polymer through an optional linker unit LX (UV absorbing chromophore $Y^2$). However, the UV absorbing chromophore may also be directly bonded to the hyperbranched polymer through a chemical bond (UV absorbing chromophore $Y^1$). Thus, if there is more than one UV absorbing chromophore present in the conjugate, some of the UV absorbing chromophores may be directly bonded to the hyperbranched polymer (i.e. UV absorbing chromophores $Y^1$), the others through the linker unit LX (i.e. UV absorbing chromophores $Y^2$). Preferably, all UV absorbing chromophores are bonded to the hyperbranched polymer through the linker unit LX (i.e. UV absorbing chromophores $Y^2$). However, when index p=0, no linker unit is present and in consequence, all UV absorbing chromophores are UV absorbing chromophores $Y^1$ which are directly bonded to the hyperbranched polymer.

The chemical nature of the UV absorbing chromophores $Y^1$ may differ from the UV absorbing chromophores $Y^2$. Preferably, however, UV absorbing chromophores $Y^1$ and $Y^2$ are identical.

The linking units LX are composed of a linker L and a functional group X. Functional group X is either capable of reacting with the UV absorbing chromophore or convertible into another functional group which is capable of reacting with the UV absorbing chromophore $Y^2$ in a subsequent reaction step.

In a preferred embodiment of the present invention the linker L is a polymer, such as polyethylene, polypropylene, polyacrylates, polymethacrylates, polyvinylalcohols, polyvinyl esters, polyvinyl ethers, polyurethanes, polyurea, polyisocyanates, polyvinyl pyridines, polyvinyl pyrrolidones, polyethers such as polyethylene glycol and polypropylene glycol, polyethylene imines, polycarbonates, polyesters and polycaprolactones, polyamides, styrene-acrylonitrile copolymers (SAN), styrene-maleic anhydride copolymers (SMA) and polyphenylene oxide. In a preferred embodiment the polymeric linker L is polymerized on the hyperbranched polymer such that the individual polymeric linkers L on the hyperbranched polymer exhibit variable degrees of polymerization. Preferably, the linker unit LX is polyethyleneoxide ([PEO]-OH) or polypropyleneoxide ([PPO]-OH). Preferably, the linker L is polyethyleneoxide or polypropyleneoxide having an average degree of polymerization $DP_n$ within the range of from 1 to 100, preferably 10 to 80, more preferably 15 to 70, most preferably 20 to 60.

In another preferred embodiment of the present invention the linker L is an ω-alkyldiol, ω-alkyldiamine, ω-alkyldithiol or an ω-alkyldicarboxylic acid. Preferably, the linker L is an ω-alkyldiol. The number of carbon atoms in these groups is preferably 1 to 20.

In another preferred embodiment of the present invention the linker unit LX is a group

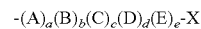

-$(A)_a(B)_b(C)_c(D)_d(E)_e$-X wherein
  A is CONH, O, S or NH;
  B is a linear or branched alkylene group with up to 20, preferably 1-12, most preferably 3-12 carbon atoms;
  C is O, S or NH;
  D is CONH;
  E is a linear or branched alkylene, alkenylene or alkynylene group with up to 20, preferably 1-12, most preferably 3-12 carbon atoms; and
  index a is 0 or 1;
  index b is 0 or 1;
  index c is 0 or 1;
  index d is 0 or 1; and
  index e is 0 or 1;
  with the proviso that at least one of indices b and e is 1.

Preferred functional groups X are —CH=$CH_2$, —C≡CH, —OH, —$NH_2$, —NH—$C_1$-$C_6$-alkyl, —$NHNH_2$, —COCl, —$CO_2H$, —$CON_3$, —CHO, —SH, —$SO_2Cl$, —$SO_3H$, —Cl, —Br, —I, —NCO, —NCS, —SCN, maleimide, oxirane and thiirane. In a particularly preferred embodiment of the present invention the functional group X is —OH.

A functional group X may either be covalently bonded to an UV absorbing chromophore $Y^2$, covalently bonded to a capping group, or be in its free reactive form. Depending on their chemical nature, the reactive form of functional groups X may cause problems when the conjugates are to be applied to human skin or hair. In such cases the functional groups X which are not covalently bonded to an UV absorbing chromophore $Y^2$, are preferably capped. Suitable capping agents are capable of reacting with functional groups X and result in a capped linker unit LX. The skilled person is aware of suitable capping agents which can be used to introduce the corresponding capping groups. For example, if functional group X is —$NH_2$ or —OH it may be acetylated (capping group) by means of e.g. acetanhydride or acetylchloride (capping agent).

In a preferred embodiment of the present invention the conjugate comprises a structure represented by general formula (II)

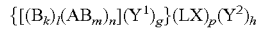 (II), wherein
Y$^1$ and Y$^2$ are defined as above;
LX is defined as above;
B$_k$ represents a starter unit bearing k functional groups B, wherein independently each functional group B is
  covalently bonded to a functional group A of a building block AB$_m$, or
  covalently bonded to the proximal end of a linker unit LX, or
  covalently bonded to an UV absorbing chromophore Y$^1$, or
  covalently bonded to a capping group, or
  in its free reactive form;
(AB$_m$)$_n$ represents n building blocks AB$_m$, each bearing a functional group A and m independent functional groups B, wherein independently each functional group A is
  covalently bonded to a functional group B
    of a further building block AB$_m$ or
    of the starter unit B$_k$, or (particularly when index l is 0:)
  covalently bonded to a capping group, or
  in its free reactive form,
  and wherein independently each functional group B is
    covalently bonded to a functional group A of a further building block AB$_m$, or
    covalently bonded to the proximal end of a linker unit LX, or
    covalently bonded to an UV absorbing chromophore Y$^1$, or
    covalently bonded to a capping group, or
    in its free reactive form;
wherein
  index g is defined as above;
  index h is defined as above
  index k is an integer of from 1 to 6, preferably from 2 to 5, more preferably 3 or 4;
  index l is 0 or 1;
  index m is an integer of from 2 to 4, preferably 2 or 3;
  index n is an integer of from 3 to 100, preferably 10 to 80, more preferably 25 to 50; and
  index p is an integer wherein $0 \leq p \leq n(m-1)+k$.

A functional group B may either be covalently bonded to a functional group A of a building block AB$_m$, to the proximal end of a linker unit LX, to an UV absorbing chromophore Y$^1$, or to a capping group, or be in its free reactive form. Depending on their chemical nature, the reactive form of functional groups B may cause problems when the conjugates are to be applied to human skin or hair. In such cases the functional groups B, which are neither covalently bonded to a functional group A of a building block AB$_m$, nor to the proximal end of a linker unit LX, nor to an UV absorbing chromophore Y$^1$, are preferably capped. Suitable capping agents are capable of reacting with functional groups B and result in capped building blocks AB$_m$ and/or starter units B$_k$. The skilled person is aware of suitable capping agents which can be used to introduce the corresponding capping groups. For example, if functional group B is —$NH_2$ or —OH it may be acetylated (capping group) by means of e.g. acetanhydride or acetylchloride (capping agent). The same applies to functional group A, particularly when index l is 0.

If capping groups are present in the conjugates of the present invention, preferably 1 to 20 capping groups are present, more preferably 1 to 10. The capping group is preferably a straight or a branched ether or ester group containing preferably 1 to 20 carbon atoms, more preferably 5 to 16 carbon atoms.

Preferably, the hyperbranched polymer is composed of an optional starting unit B$_k$ and a single type of building block AB$_m$. Preferably, the index m is 2 or 3.

In a preferred embodiment of the present invention, the functional groups A and B of the building block AB$_m$ are complementary, i.e. functional groups A are capable of reacting with functional groups B but not with functional groups A, and functional groups B are capable of reacting with functional groups A but not with functional groups B. Preferred pairs of complementary functional groups A and B in building blocks AB$_m$ (or in the inverted case BA$_m$) are:

| functional group A | functional group B |
|---|---|
| HO$_2$C— | HO— |
| HO$_2$C— | H$_2$N— |
| (HO)$_2$B-aryl | Br-aryl |
| H-alkynyl | I-aryl |
| H—Si | H$_2$C=CH—CH$_2$—Si |
| HO-aryl | F-aryl |
| ClCO-aryl | (H$_3$C)$_3$SiO-aryl |
| cyclo-CO—O—CO— | HO— |
| cyclo-CO—O—CO— | H$_2$N— |
| epoxide | OH |
| epoxide | NH$_2$ |
| epoxide | SH |
| isocyanate | OH |
| isocyanate | NH$_2$ |
| isocyanate | SH |
| thioisocyanate | OH |
| thioisocyanate | NH$_2$ |
| thioisocyanate | SH |
| anhydride | OH |
| anhydride | NH$_2$ |
| anhydride | SH |
| COCl | OH |
| COCl | NH$_2$ |
| COCl | SH |

Building blocks AB$_m$ comprise one functional group A and m independent functional groups B. This means that, for the purpose of the present specification, the building block AB$_m$ in its reactive form may comprise the functional groups B in different modes:

For example, epoxides such as glycidol are a preferred building block of the AB$_2$-type. In basic medium the primary hydroxy group of glycidol is deprotonated thereby initiating an anionic ring-opening multibranching polymerization (ROMBP):

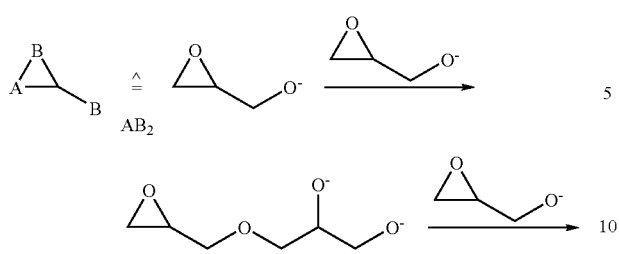

Thus, in glycidol the electrophilic carbon atom of the oxirane is functional group A. However, functional groups B are represented by the alcoholate of deprotonated glycidol as well as the alcoholate deliberated upon ring opening (which is initiated by the nucleophilic attack of another deprotonated glycidol on the electrophilic carbon atom of the oxirane).

Other suitable epoxides are ethylene oxide and propylene oxide. Lactones, lactams, cyclic amines such as aziridine and cyclic ethers such as furan can react similar to the glycidol as shown above.

Figure 4:
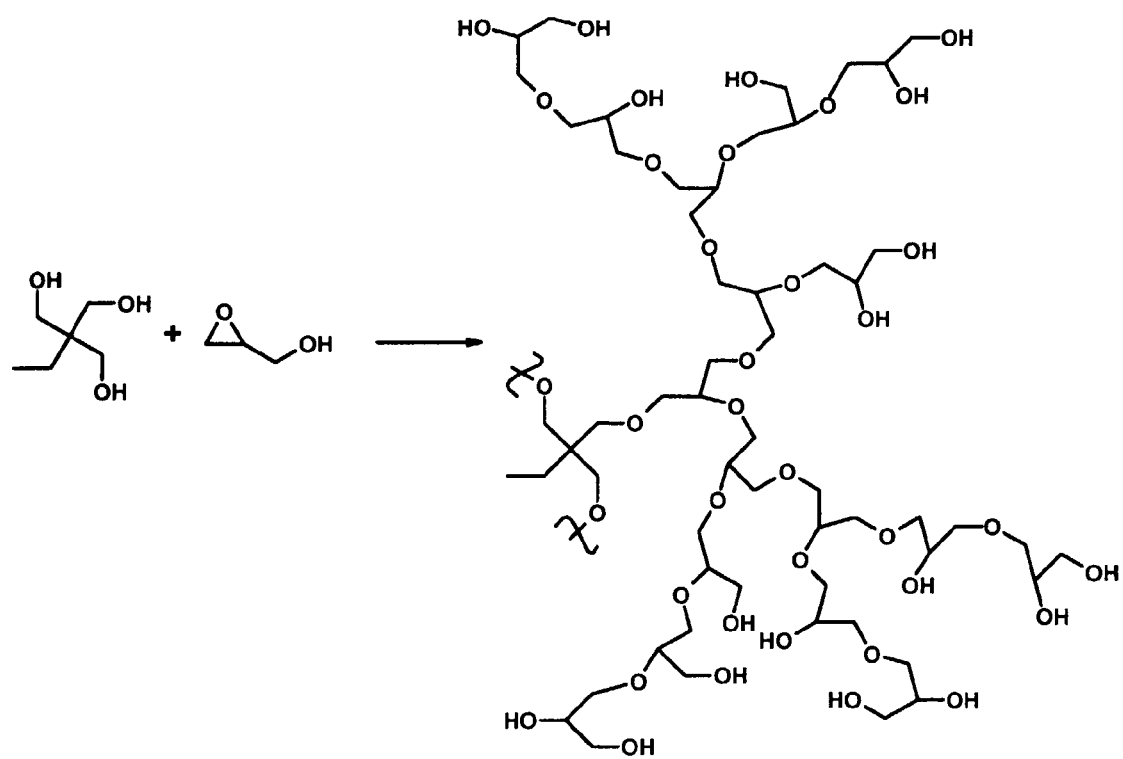

An example of a reaction of glycidol as a building block of the $AB_2$-type with trimethylol propane as starter unit is shown in FIG. 4. Thus, FIG. 4 shows an example of a non-dendritic hyperbranched polymer of the type shown in FIG. 1.

For the purpose of the present specification a building block of the $AB_m$-type comprises all building blocks in which the reactive forms of functional groups B are present in different modes. When a hyperbranched polymer is defined by a certain building block $AB_m$ in its reactive, monomeric form, the skilled person will be aware of the chemical linkage of functional groups A and B within the hyperbranched polymer (e.g. —$CO_2H$+—$NH_2$ corresponds to —CONH—).

The following building blocks of the $AB_2$-type are preferred (cf. A. Sunder et al., Chem. Eur. J. 2000, 6, 2499-2506):

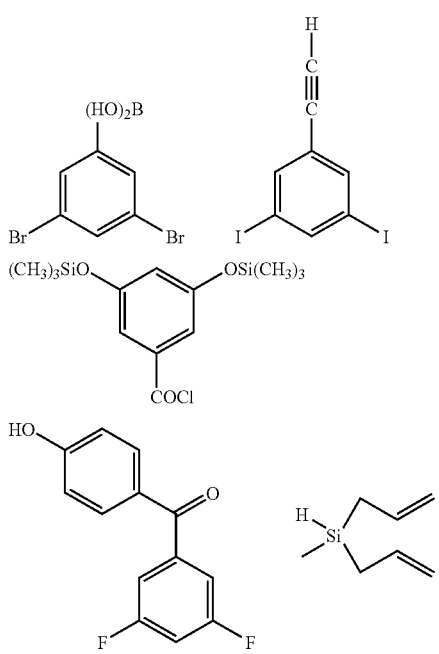

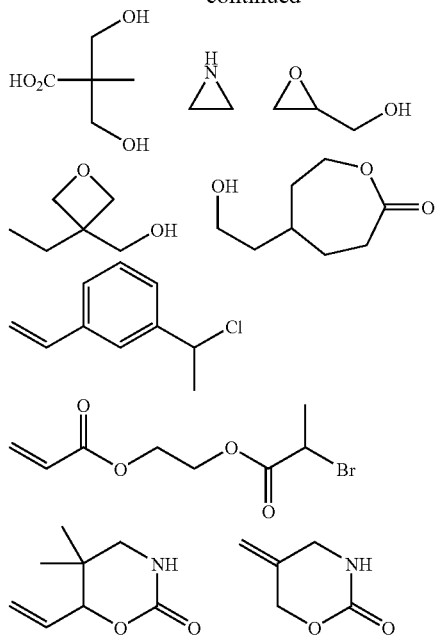

In a preferred embodiment of the present invention the conjugate is represented by general formula (II), wherein index l is 1, the starting unit $B_k$ is trimethylolpropane and the building block $AB_m$ is glycidol. Such a structure is principally shown in FIG. 4 (without the chromophores).

In another preferred embodiment of the present invention the conjugate comprises a structure represented by general formula (III)

$$\{[(B_k)_l(AB_m)_n(C_q)_r](Y^1)_g\}(LX)_p(Y^2)_h \quad (III),$$

wherein
  $Y^1$ and $Y^2$ are defined as defined above;
  LX is defined as above;
  $B_k$ represents a starter unit bearing k functional groups B,
    wherein independently each functional group B is
      covalently bonded to a functional group C
        of a monomer $C_2$ or
        of a building block $C_q$ or
      covalently bonded to the proximal end of a linker unit LX, or
      covalently bonded to an UV absorbing chromophore $Y^1$, or
      covalently bonded to a capping group, or
      in its free reactive form;
  $(AB_m)_n$ represents n building blocks $AB_m$, each bearing a functional group A and m independent functional groups B, wherein independently each functional group A is
      covalently bonded to a functional group C
        of a monomer $C_2$ or
        of a building block $C_q$, or
      covalently bonded to the proximal end of a linker unit LX, or
      covalently bonded to an UV absorbing chromophore $Y^1$, or
      covalently bonded to a capping group, or
      in its free reactive form;
  and wherein independently each functional group B is
      covalently bonded to a functional group C
        of a monomer $C_2$ or
        of a building block $C_q$, or covalently bonded to the proximal end of a linker unit LX, or covalently bonded to an UV absorbing chromophore $Y^1$, or covalently bonded to a capping group, or in its free reactive form;

$(C_q)_r$ represents when index q=2: r monomers $C_2$ or when index q>2: r building blocks $C_q$ each bearing q functional groups C, wherein independently each functional group C is covalently bonded to a functional group A of a building block $AB_m$, or covalently bonded to a functional group B of a building block $AB_m$ or of the starter unit $B_k$, or covalently bonded to the proximal end of a linker unit LX, or covalently bonded to an UV absorbing chromophore $Y^1$, or covalently bonded to a capping group, or in its free reactive form;

wherein index g is defined as above;

index h is defined as above;

index k is an integer of from 1 to 6, preferably from 2 to 5, more preferably 3 or 4;

index l is 0 or 1;

index m is an integer of from 2 to 4, preferably 2 or 3;

index n is an integer of from 3 to 100, preferably 10 to 80, more preferably 25 to 50;

index p is an integer wherein $0 \leq p \leq n(m-1)+r(q-1)+k$;

index q is an integer of from 2 to 4, preferably 2 or 3; and index r is an integer wherein $1 \leq r \leq nm/q$.

Preferably, index l is 0, index q is 2, building block $AB_m$ is a compound wherein functional group A is —NH— and functional group B is —OH, preferably diisopropanolamine, and monomer $C_2$ is a compound represented by general formula (IV)

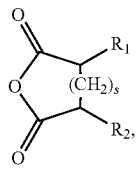

(IV)

wherein index s is 0, 1 or 2, preferably 0;

$R^1$ and $R^2$ are independently H, linear or branched $C_1$-$C_{18}$-alkyl or $C_2$-$C_{18}$-alkenyl, or $R_1$ and $R_2$ together with the carbon atoms to which the are attached form a 4 to 7 membered aliphatic or aromatic ring. Preferably $R^1$ is H and $R^2$ is $C_{12}$-alkyl.

In a preferred embodiment of the present invention the hyperbranched polymer is composed of a building block $AB_2$ selected from the group consisting of the following bis-(hydroxy)amines

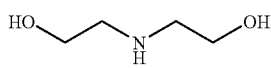

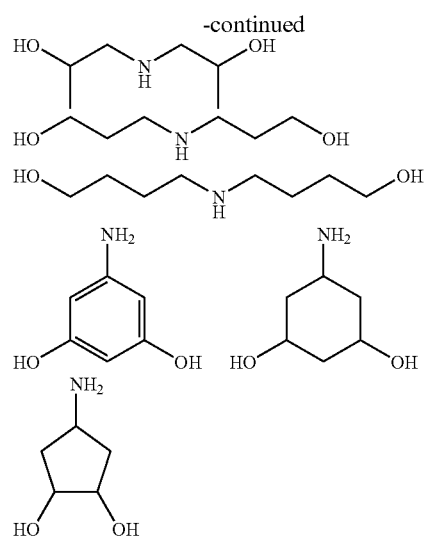

in combination with a monomer of the $C_2$-type selected from the group consisting of the following anhydrides:

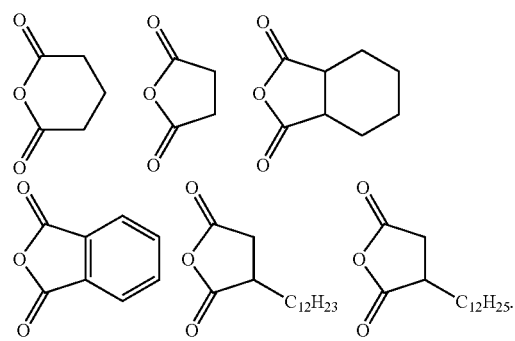

Preferably, the double bond in the $C_{12}H_{23}$ group is in β-position.

The UV absorbing chromophores covalently bonded to the hyperbranched polymers comprise all groups which absorb light in the range of wavelengths 400 nm to 320 nm (UV-A) and 320 nm to 290 nm (UV-B) or of even shorter wavelengths (UV-C) and which are or can be used as chemical UV filters. These groups are, e.g., residues of compounds belonging to the groups of acrylates, p-aminobenzoates, camphor derivatives (such as of benzylidene camphor type), cinnamates, benzophenones, esters of benzalmalonic acid, esters of 2-(4-ethoxy anilinomethylene)propandioic, imidazole derivatives, salicylates, triazone derivatives, triazol derivatives, dibenzoylmethanes, amino substituted hydroxybenzophenones, phenyl-benzimidazoles, anthranilates, phenyl-benzoxazoles, 1,4-dihydropyranes and others representing state of the art and known to those skilled in the art to be highly active.

Examples for acrylates include 2-ethylhexyl 2-cyano-3,3-diphenylacrylate (octocrylene, PARSOL® 340) and ethyl 2-cyano-3,3-diphenylacrylate.

Examples for p-aminobenzoates include 4-amino benzoic acid, 4-aminobenzoic acid-2,3-dihydroxypropylester, 4-(bis(2-hydroxypropyl)amino)benzoic acid ethyl ester, 4-(dimethyl-amino)benzoic acid-2-ethylhexylester (e.g. Eusolex® 6007) and ethoxylated 4-aminobenzoic acid ethyl ester (e.g. Uvinul® P25).

Examples for camphor derivatives include 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor and therephthalidene dicamphor sulfonic acid.

Examples for cinnamates include octyl methoxycinnamate (PARSOL® MCX), ethoxyethyl methoxycinnamate, diethanolamine methoxycinnamate (PARSOL® Hydro) and isoamyl methoxycinnamate.

Examples for benzophenones include benzophenone-3, benzophenone-4,2,2',4,4'-tetra-hydroxy-benzophenone and 2,2'-dihydroxy-4,4'dimethoxybenzophenone.

Examples for esters of benzalmalonic acid include di(2-ethylhexyl) 4-methoxybenzal-malonate.

Examples for esters of 2-(4-ethoxy anilinomethylene)propandioic acid include 2-(4-ethoxy anilinomethylene)propandioic acid diethyl ester as described in EP-A 895 776.

Examples for imidazole derivatives include 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts and diethanolamine salts.

Examples for salicylate derivatives include isopropylbenzyl salicylate, benzyl salicylate, butyl salicylate, octyl salicylate (NEO HELIOPAN OS), isooctyl salicylate or homomenthyl salicylate (homosalate, HELIOPAN).

Examples for triazone derivatives include octyl triazone (UVINUL T-150), dioctyl butamido triazone (UVASORB HEB).

Examples for triazol derivatives include benzotriazoles such as 2-(2-hydroxy-5-methylphanyl)benzotriazol, 2,2'-methylene-bis-(6-(2H-benzotriazole-2-yl)-4-(1,1,3,3,-tetra-methylbutyl)-phenol (TINOSORB M) as well as triazols described in EP-A 893 119.

Examples for dibenzoylmethane derivatives include compounds such as 4-tert. butyl-4'-methoxydibenzoyl-methane (PARSOL® 1789), dimethoxydibenzoylmethane and isopropyl-dibenzoylmethane.

Examples for amino substituted hydroxybenzophenones include compounds such as 2-(4-Diethylamino-2-hydroxy-benzoyl)-benzoic acid hexyl ester as described in EP-A 1 046 391.

Preferred UV absorbing chromophores are
Benzophenone derivatives such as

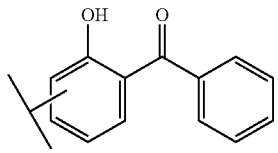

p-Aminobenzoic acid derivatives such as

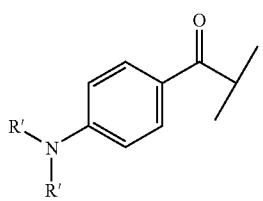

Benzoxazole derivatives such as

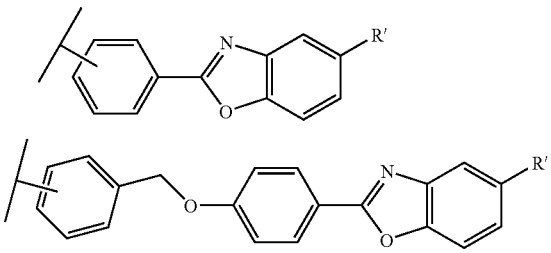

Camphor derivatives such as

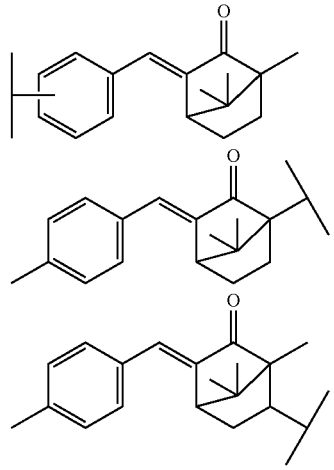

Cinnamic acid or benzalmalonate derivatives such as

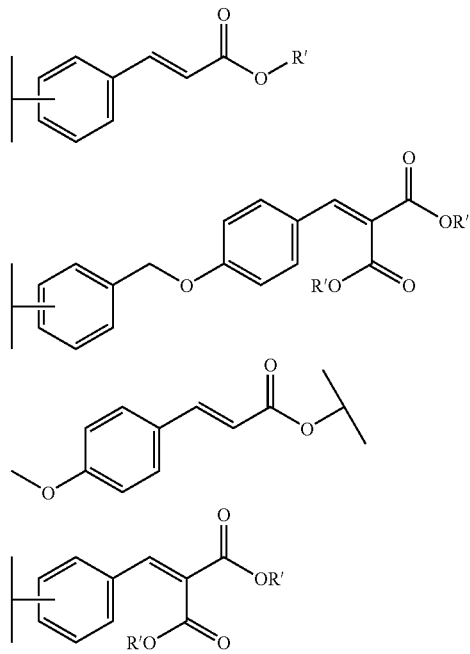

Benzimidazole derivatives such as

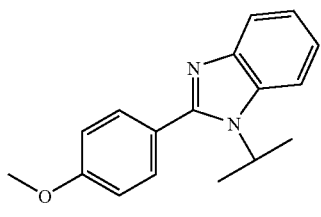

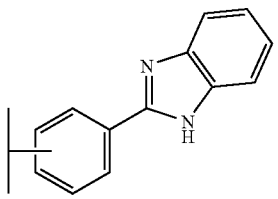

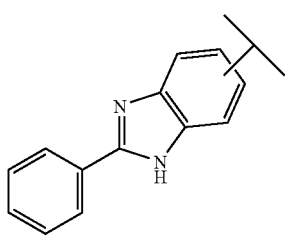

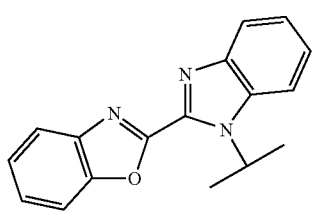

Octocrylene derivatives such as

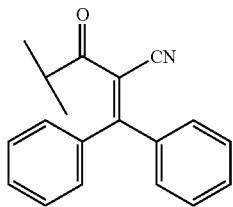

Benzotriazol derivatives such as

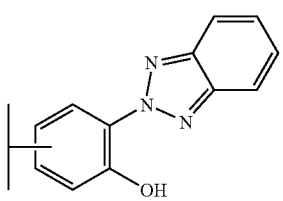

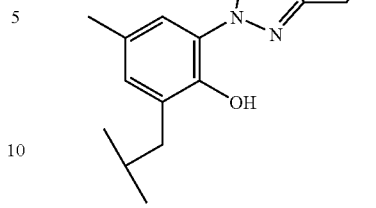

Dihydropyridine Derivatives such as

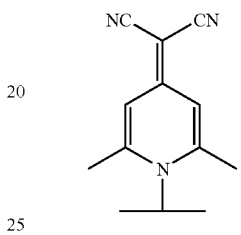

tert-Butyldibenzoylmethane derivatives such as

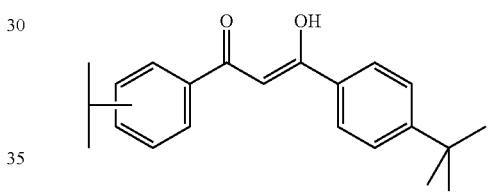

wherein R' is H, OH, straight or branched chain $C_1$-$C_{20}$-alkyl, $C_1$-$C_{20}$-alkoxy or $C_{2-20}$-alkenyl.

In the above chemical structures "−" denotes the linkage to the hyperbranched polymer.

Preferably, the UV absorbing chromophore is a compound selected from the group consisting of the compounds represented by general formulae (V-A) to (V-E)

(V-A)
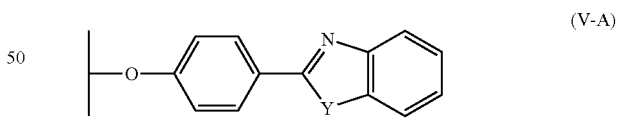

(V-B)
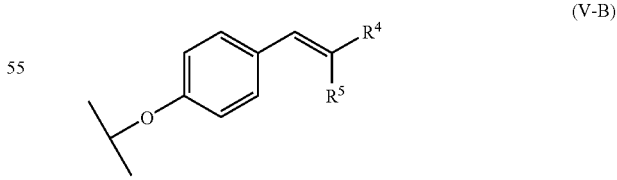

(V-C)
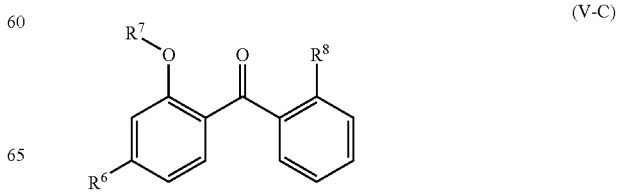

-continued

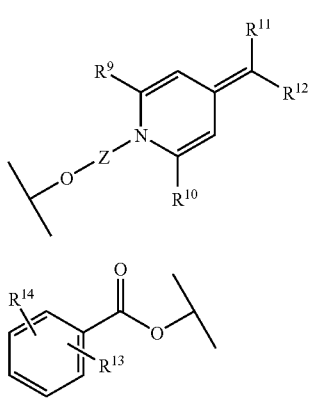
(V-D)

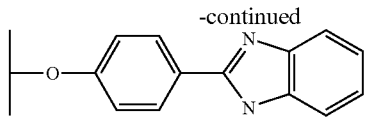
(V-E)

wherein
- Y is O or $NR^3$ wherein $R^3$ is H, $C_1$-$C_6$-alkyl or $C_2$-$C_6$-alkenyl;
- $R^4$ and $R^5$ are independently H, $C_1$-$C_6$-alkyl, $C_2$-$C_6$-alkenyl, $CO_2H$, $CO_2$—$C_1$-$C_6$-alkyl, preferably $CO_2Et$, or $R^4$ and $R^5$ together with the carbon atom to which they are attached form a 6-camphenyl ring;
- $R^6$ is hydrogen, $C_1$-$C_6$-alkyl, $C_2$-$C_6$-alkenyl or O-⊣, preferably H or O-⊣;
- $R^7$ is H, $C_1$-$C_6$-alkyl or $C_2$-$C_6$-alkenyl;
- $R^8$ is H or CO—O-⊣;
- $R^9$ and $R^{10}$ are independently H or $C_1$-$C_6$-alkyl, preferably methyl;
- $R^{11}$ and $R^{12}$ are independently H, $C_1$-$C_6$-alkyl, $NO_2$, $CO_2$—$C_1$-$C_6$-alykl or CN, preferably CN;
- Z is $C_1$-$C_6$-alkylene, preferably ethylene;
- $R^{13}$ and $R^{14}$ are independently H, $OR^{15}$, $NR^{16}R^{17}$ or $C_1$-$C_6$-alkyl, preferably methyl;
- $R^{15}$, $R^{16}$ and $R^{17}$ are independently H or $C_1$-$C_6$-alkyl, preferably H;
- $R^{16}$ and $R^{17}$ are preferably methyl and $R^{15}$ is preferably H.

Residue (V-E) is preferably a residue

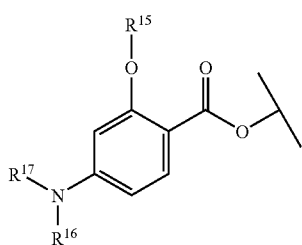

In the above definition "-⊣" denotes the linkage to the hyperbranched polymer.

The following UV absorbing chromophores are particularly preferred:

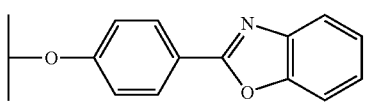

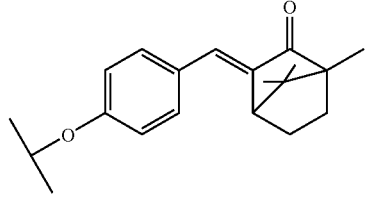

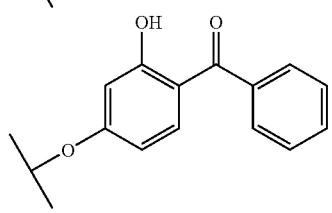

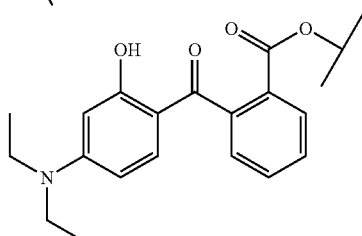

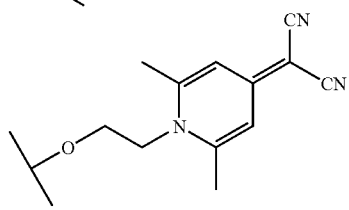

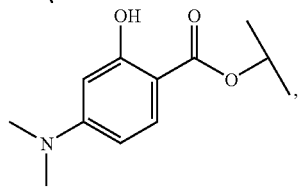

wherein R is H, OH, straight or branched chain $C_1$-$C_{20}$-alkyl, $C_1$-$C_{20}$-alkoxy or $C_{2-20}$-alkenyl.

The photostability of the conjugates according to the present invention may be measured according to G. Berset et al. International Journal of Cosmetic Science 1996, 18(3), 167-177.

The conjugates according to the present invention are particularly useful as UV sunscreens.

The present invention also relates to compositions, preferably to cosmetic compositions comprising a conjugate as described above and a cosmetically acceptable carrier.

The compositions according to the present invention may comprise one or more of the conjugates as described above. In a preferred embodiment of the present invention the composition comprises two different conjugates, the first being a hyperbranched polymer covalently bonded to an UV absorbing chromophore having an UV absorption maximum 280 nm$\leq \lambda_{max} \leq$320 nm, the second being the same or a different hyperbranched polymer covalently bonded to another UV absorbing chromophore having an UV absorption maximum 320 nm$\leq \lambda_{max} \leq$400 nm.

Preferably, the compositions according to the present invention may also contain usual cosmetic adjuvants and additives, such as preservatives/antioxidants, fatty substances/oils, water, organic solvents, silicones, thickeners, softeners, emulsifiers, additional sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, in particular those suited for providing an additional photoprotective effect by physically blocking out ultraviolet radiation, or any other ingredients usually contained in cosmetics, in particular for the production of sunscreen/antisun compositions. The necessary amounts of the cosmetic and dermatological adjuvants and additives can, based on the desired product, easily be chosen by a skilled artisan in this field.

An additional amount of antioxidants/preservatives is generally preferred. According to the present invention all known antioxidants usually contained in cosmetics can be used. Especially preferred are antioxidants selected from the group consisting of amino acids (e.g. glycine, histidine, tyrosine, tryptophane) and their derivatives, imidazole (e.g. urocanic acid) and its derivatives, peptides such as D,L-carnosine, D-carnosine, L-carnosine and their derivatives (e.g. anserine), carotenoids, carotenes (e.g. α-carotene, β-carotene, lycopene) and their derivatives, chlorogenic acid and its derivatives, lipoic acid and its derivatives (e.g. dihydrolipoic acid), aurothioglucose, propylthiouracil and other thiols (e.g. thioredoxine, glutathione, cysteine, cystine, cystamine and its glycosyl-, N-acetyl, methyl-, ethyl-, propyl-, amyl-, butyl-, lauryl-, palmitoyl, oleyl-, γ-linoleyl-, cholesteryl- and glyceryl-ester) and the salts thereof, dilaurylthiodipropionate, distearylthiodipropionate, thiodipropionic acid and its derivatives (e.g. its esters, ethers, peptides, lipids, nucleotides, nucleosides and salts) as well as sulfoximine derivatives (such as buthioninsulfoximine, homocysteinsulfoximine, buthioninsulfone, penta-, hexa-, heptathioninsulfoximine) in very low compatible doses (e.g. pmol kg$^{-1}$ to μmol kg$^{-1}$), additionally (metal)-chelators (such as γ-hydroxyfatty acids, palmic acid, phytinic acid and lactoferrin), β-hydroxyacids (such as citric acid, lactic acid and malic acid), huminic acid, gallic acid, gallic extracts, bilirubin, biliverdin, EDTA, EGTA and their derivatives, unsaturated fatty acids and their derivatives (such as γ-linoleic acid, linolic acid and oleic acid), folic acid and its derivatives, ubiquinone and ubiquinol and their derivatives, vitamin C and its derivatives (such as ascorbylpalmitate, ascorbyltetraisopalmitate, Mg-ascorbylphosphate, Na-ascorbylphosphate and ascorbylacetate), tocopherol and its derivatives (such as vitamin-E-acetate), mixtures of natural vitamin E, vitamin A and their derivatives (such as palmitate-A-palmitate and -acetate) as well as coniferylbenzoate, rutinic acid and their derivatives, α-glycosylrutin, ferulic acid, furfurylidenglucitol, carnosin, butylhydroxytoluene, butylhydroxyanisole, trihydroxybutyrophenone, urea and their derivatives, mannose and its derivatives, zinc and its derivatives (e.g. zinc salts such as ZnO, ZnSO$_4$), selen and its derivatives (e.g. selenomethionin), stilbenes and their derivatives (such as stilbenoxide, trans-stilbenoxide) and suitable derivatives thereof (e.g. salts, esters, ethers, glycosides, nucleotides, nucleosides, peptides and lipids) of the preceding active ingredients. Preferably, one or more preservatives/antioxidants may be present in an amount of about 0.01 wt.-% to about 10 wt.-% of the total weight of the composition of the present invention. More preferably, one or more preservatives/antioxidants are present in an amount of about 0.1 wt.-% to about 1 wt.-%.

Preferably, the compositions according to the present invention also contain surface active ingredients like emulsifiers, solubilizers and the like. An emulsifier enables two or more immiscible components to be combined homogenously. Moreover, the emulsifier acts to stabilize the composition. Emulsifiers that may be used in the compositions according to the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6-hexaricinolate, polyglyceryl-4-oleate, polyglyceryl-4-oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as emulsifier. For example, PVP eicosene copolymer, acrylates/C$_{10-30}$-alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP eicosene copolymer, acrylates/C$_{10-30}$-alkyl acrylate crosspolymer, PEG-20 sorbitan isostearate, sorbitan isostearate, and mixtures thereof. The one or more emulsifiers are preferably present in a total amount of about 0.01 wt.-% to about 20 wt.-% of the total weight of the composition according to the present invention. More preferably, about 0.1 wt.-% to about 10 wt.-% of emulsifiers are used.

Preferably, the lipid phase may be selected from:
mineral oils and mineral waxes;
oils such as triglycerides of caprinic acid or caprylic acid, preferably castor oil;
oils or waxes and other natural or synthetic oils, preferably esters of fatty acids with alcohols e.g. isopropanol, propyleneglycol, glycerin or esters of fatty alcohols with carboxylic acids or fatty acids;
alkylbenzoates; and/or
silicone oils such as dimethylpolysiloxane, diethylpolysiloxane, diphenylpolysiloxane, cyclomethicones and mixtures thereof.

Preferred examples of fatty substances which may be incorporated in the oil phase of the emulsion, microemulsion, oleo gel, hydrodispersion or lipodispersion of the composition according to the present invention are selected from esters of saturated and/or unsaturated, linear and/or branched alkyl carboxylic acids having 3 to 30 carbon atoms, and saturated and/or unsaturated, linear and/or branched alcohols having 3 to 30 carbon atoms as well as esters of aromatic carboxylic acids and of saturated and/or unsaturated, linear and/or branched alcohols having 3 to 30 carbon atoms. Preferably, such esters may be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaureate, n-decyloleate, isooctylstearate, isononylstearate, isononylisononanoate, 2-ethylhexylpalmitate, 2-ethylhexyllaurate, 2-hexyl-decylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters, e.g. jojoba oil.

Further preferred fatty components suitable for use in the composition according to the present invention include polar oils such as lecithins and fatty acid triglycerides, namely triglycerol esters of saturated and/or unsaturated, linear or branched carboxylic acids having 8 to 24 carbon atoms, preferably of 12 to 18 carbon atoms, whereas the fatty acid triglycerides are preferably selected from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes, e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicone (octamethylcyclotetrasiloxane; cetyldimethicone, hexamethylcyclotrisiloxane, polydimethylsiloxane, poly(methylphenylsiloxane) and mixtures thereof.

Further fatty components which preferably may be incorporated in the composition according to the present invention are isoeicosane; neopentylglycoldiheptanoate; propylenegly-coldicaprylate/dicaprate; caprylic/capric/diglycerylsuccinate; butyleneglycol caprylat/caprat; $C_{12-13}$-alykllactate; di-$C_{12-13}$-alkyltartrate; triisostearin; dipentaerythrityl hexacaprylat/hexacaprate; propyleneglycolmonoisostearate; tricaprylin; dimethylisosorbid. Especially beneficial is the use of mixtures of $C_{12-15}$-alkylbenzoate and 2-ethylhexylisostearate, mixtures of $C_{12-15}$-alkylbenzoate and isotridecylisononanoate as well as mixtures of $C_{12-15}$-alkylbenzoate, 2-ethylhexylisostearate and isotridecylisononanoate.

Preferably, the oily phase of the composition according to the present invention may also contain natural vegetable or animal waxes such as bee wax, china wax, bumblebee wax and other waxes of insects as well as shea butter and cocoa butter.

Preferably, a moisturizing agent may be incorporated into a composition of the present invention to maintain hydration or to rehydrate the skin. Moisturizers that prevent water from evaporating from the skin by providing a protective coating are called "emollients". Additionally, an emollient provides a softening or soothing effect on the skin surface and is generally considered safe for topical use. Preferred emollients include mineral oils, lanolin, petrolatum, capric/caprylic triglyceraldehydes, cholesterol, silicones such as dimethicone, cyclomethicone, almond oil, jojoba oil, avocado oil, castor oil, sesame oil, sunflower oil, coconut oil and grape seed oil, cocoa butter, olive oil, aloe extracts, fatty acids such as oleic and stearic acid, fatty alcohols such as cetyl and hexadecyl alcohol (ENJAY), diisopropyl adipate, hydroxybenzoate esters, benzoic acid esters of $C_{9-15}$-alcohols, isononyl isononanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient is preferably present in an amount of about 1 wt.-% to about 20 wt.-% of the total weight of the composition. More preferably the content of the emollient ranges from about 2 wt.-% to about 15 wt.-%, and most preferably from about 4 wt.-% to about 10 wt.-% of the total weight of the composition.

Moisturizers that bind water, thereby retaining it on the skin surface are called "humectants". Preferably, suitable humectants may be incorporated into a composition according to the present invention such as glycerin, polypropylene glycol, polyethylene glycol, lactic acid, pyrrolidone carboxylic acid, urea, phospholipids, collagen, elastin, ceramides, lecithin sorbitol, PEG-4, and mixtures thereof. Additional suitable moisturizers are polymeric moisturizers of the family of water soluble and/or swellable and/or with water gelating polysaccharides such as hyaluronic acid, chitosan and/or a fucose rich polysaccharide which is e.g. available as Fucogel® 1000 (CAS-Nr. 178463-23-5) by SOLABIA S. Preferably, one or more humectants are optionally present in an amount of about 0.5 wt.-% to about 8 wt.-% in a composition according to the present invention, preferably of about 1 wt.-% to about 5 wt.-%.

Preferably, the aqueous phase of the composition according to the present invention may contain usual cosmetic additives such as alcohols, especially lower alcohols, preferably ethanol and/or isopropanol, low diols or polyols and their ethers, preferably propyleneglycol, glycerin, ethyleneglycol, ethyleneglycol monoethyl- or monobutylether, propyleneglycol monomethyl- or monoethyl- or -monobutylether, diethyleneglycol monomethyl- or monoethylether and analogue products, polymers, foam stabilizers; electrolytes and especially one or more thickeners. Thickeners that may be preferably used in compositions according to the present invention to assist in making the consistency of a product suitable include carbomer, siliciumdioxide, magnesium and/or aluminium silicates, beeswax, stearic acid, stearyl alcohol polysaccharides and their derivatives such as xanthan gum, hydroxypropyl cellulose, polyacrylamides, acrylate crosspolymers, preferably a carbomer, such as carbopole of type 980, 981, 1382, 2984, 5984 alone or mixtures thereof. Suitable neutralizing agents which may be included in the composition according to the present invention to neutralize components such as an emulsifier or a foam builder/stabilizer include but are not limited to alkali hydroxides such as sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt.-% to about 8 wt.-% in the composition according to the present invention, preferably, 1 wt.-% to about 5 wt.-%.

The addition of electrolytes into the composition of the present invention may assist to change the behavior of a hydrophilic emulsifier. Thus, the emulsions/microemulsions according to the present invention may preferably contain electrolytes of one or several salts including anions such as chloride, sulfate, carbonate, borate and aluminate, without being limited thereto. Other suitable electrolytes may be derived from organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Preferably, the electrolytes may be present in an amount of about 0.01 wt.-% to about 8 wt.-% in the composition according to the present invention.

The compositions according to the present invention are useful as compositions for photoprotecting the human epidermis or hair against the damaging effect of ultraviolet irradiation, as sunscreen compositions. In particular, such compositions may preferably be provided in the form of a lotion, a thickened lotion, a gel, a cream, a milk, an ointment, a powder or a solid tube stick and may optionally be packaged as an aerosol and may be provided as a mousse, foam or a spray. When the composition according to the present invention is provided for protecting the human epidermis against UV irradiation or as sunscreen composition, it can be in the form of a suspension or dispersion in solvents or fatty substances, or alternatively in the form of an emulsion or microemulsion (in particular of O/W or W/O type, O/W/O or W/O/W type), such as a cream or a milk, a vesicular dispersion, in the form of an ointment, a gel, a solid tube stick or an aerosol mousse. The emulsion may also contain anionic, nonionic, cationic or amphoteric surfactants.

The conjugates according to the present invention may be prepared by reacting a hyperbranched polymer having reactive functional groups with an UV absorbing chromophore having an UV absorption maximum ≧270 nm and having a functional group capable of reacting with the functional groups of the hyperbranched polymer.

In a preferred embodiment of the preparation of the conjugates according to the present invention a hyperbranched polymer as described in A. Sunder et al., Macromolecules 1999, 32, 4240-4246; ibid 2000, 33, 309-320 is reacted with mesylchloride in the presence of a tertiary amine or with $SOCl_2$ in order to enhance the leaving group quality of the hydroxy groups of the hyperbranched polymer (activation). The activated hyperbranched polymer is reacted e.g. with a deprotonated hydroxy group of a suitable UV absorbing chromophore in a nucleophilic substitution reaction thereby forming an ether bond.

In another preferred embodiment of the preparation of the conjugates according to the present invention a hyperbranched polymer as described in A. Sunder et al., Macromolecules 1999, 32, 4240-4246; ibid 2000, 33, 309-320 is reacted with an activated carboxylic group of a suitable UV absorbing chromophore thereby forming an ester bond.

In another preferred embodiment of the preparation of the conjugates according to the present invention a hyperbranched polymer commercialized under the trademark HYBRANE by DSM B.V. having terminal hydroxy groups (cf. FIG. 3) is esterified with p-N,N-dimethylamino-benzoic acid as UV absorbing chromophore.

The present invention is further illustrated by the following examples. These examples are illustrative only and are not intended to limit the scope of the invention in any way:

EXAMPLE 1 a) Activation of OH Groups of a Poly(glycerol-b-propylene Oxide) by Mesylation

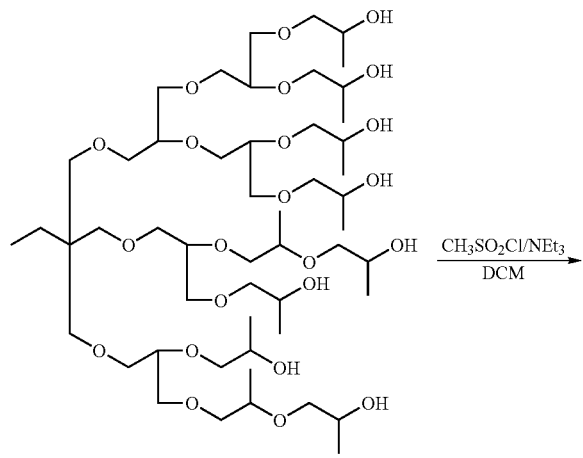

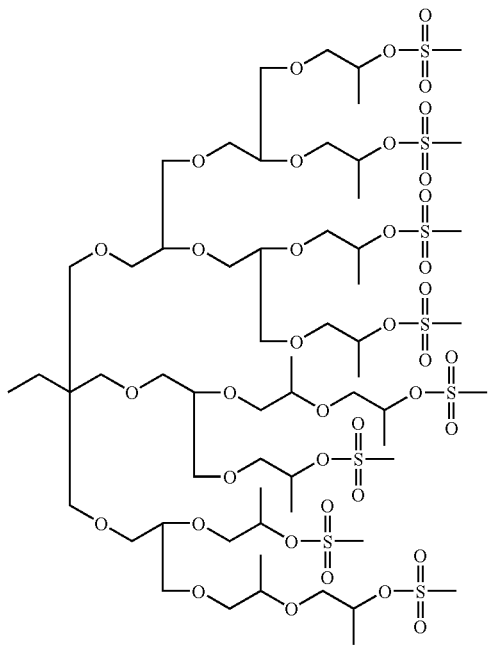

Poly(glycerol-b-propylene oxide) prepared according to Sunder, A.; Mülhaupt, R.; Frey, H. *Macromolecules*, 2000, 33, 309-314 was supplied from the Institute of Organic Chemistry of the University of Mainz, Germany. The Polyglycerol was characterized by $^1H$ NMR and GPC to reveal a PO unit/OH group ratio of 1.25 and a Mn of 1060 g/mol with a polydispersity of 1.6.

Methanesulfonyl chloride (3.75 ml, 48.5 mmol) was added dropwise to a solution of poly(glycerol-b-propylene oxide) (5.0 g, 4.6 mmol, 37 mmol OH) and triethylamine (9.5 ml, 67.9 mmol) in DCM (dichloromethane) (75 mL) under Argon at 0° C. DMAP (dimethylaminopyridine) (20 mg) was added and the mixture stirred at room temperature for 12 h. Excess of methanesulfonyl chloride was hydrolyzed by addition of water (50 mL) at 0° C. and the organic layer extracted with 2N HCl (40 mL) and water (40 mL). The combined aqueous phases were extracted with DCM (3×50 mL). The combined organic extracts were dried over sodium sulfate and filtered. Evaporation under vacuo afforded 7.5 g mesylated poly(glycerol-b-propylene oxide). Total conversion of hydroxy groups to mesyl groups was proved by the absence of OH oscillation signal at 3500-3600 $cm^{-1}$ using FT-IR analysis. The amount of mesyl groups was determined using $^1H$ NMR, comparing the integration of the signals of mesyl $CH_3$ at 3.04 ppm to trimethylolpropane $CH_3$ at 0.87 ppm, to give an average of about 8 OH/polymer.

b) Preparation of a polymeric UV-filter by attaching 4-(1,3-benzoxazol-2-yl)-phenol to an activated Poly(glycerol-b-propylene oxide)

min. A solution of mesylated poly(glycerol-b-propylene oxide) (7.48 g, 4.4 mmol, 35 mmol MsO) in NMP (60 mL) was added dropwise and the reaction mixture stirred at 80° C.

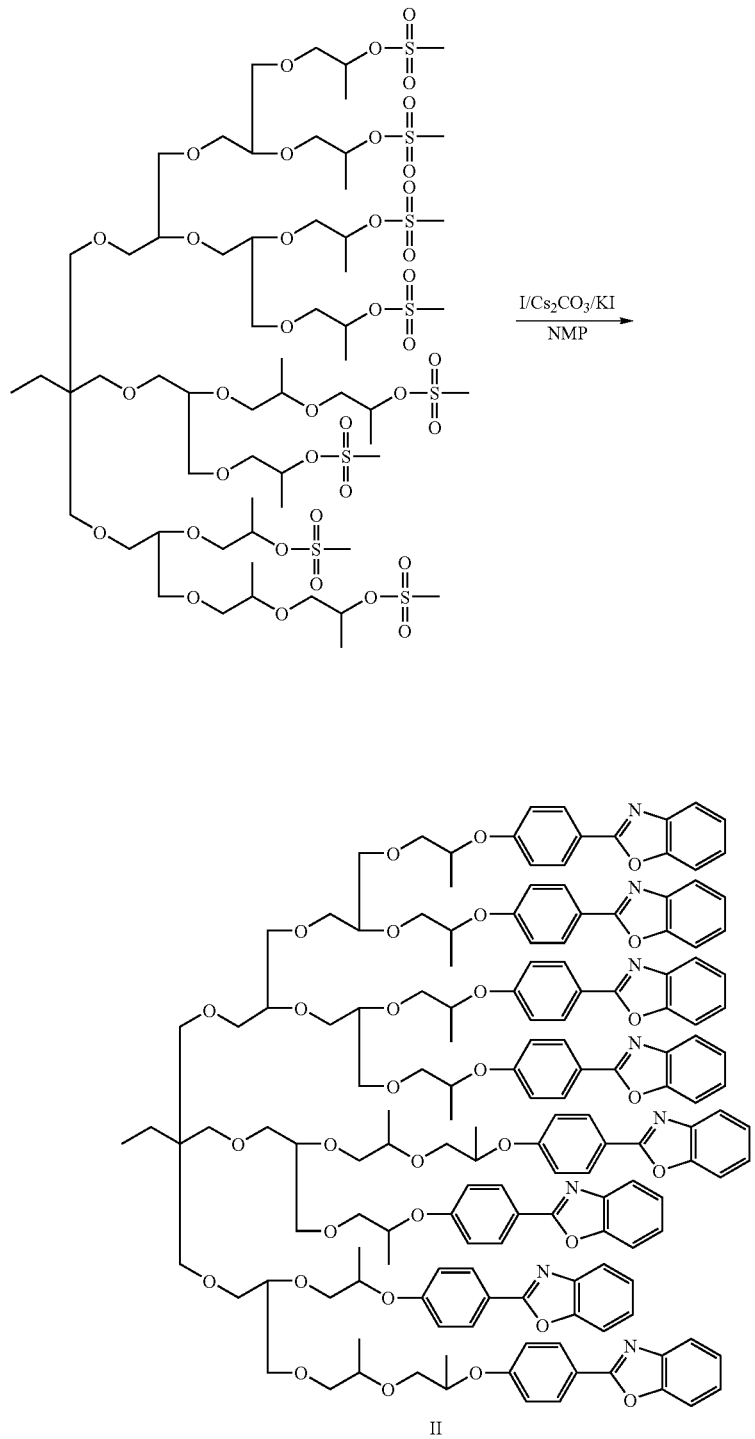

II

Cesium carbonate (16 g, 50 mmol) and potassium iodate (50 mg) were added to a solution of 4-(1,3-benzoxazol-2-yl)-phenol I (8.9 g, 42 mmol) (prepared according to Passerini, *J. Chem. Soc.* 1954, 2256-2257) in NMP (N-methylpyrolidon) (100 mL) and the mixture stirred under Argon at 80° C. for 20 for 12 h. Water and ethyl acetate were added (200 mL each), an orange precipitate was separated by filtration, and the aqueous layer was extracted with ethyl acetate (2×100 mL). The combined organic phases were washed with 2 N HCl (100 mL) and saturated bicarbonate solution (100 mL) and the combined aqueous layers extracted with ethyl acetate (100 mL). The combined organic phases were dried over sodium sulfate, filtered and evaporated under vacuo. The oily residue was purified by column chromatography (ethyl acetate/n-hexane, 1:2⇒ethyl acetate) on silica to yield 4.82 g chromophore II. The amount of attached chromophore was determined using $^1$H NMR, comparing the integration of the signals of the phenol's aromatic protons at 6.99 and 8.12 ppm to trimethylolpropane $CH_3$ at 0.87 ppm, to give an average of about 8 chromophores/polymer. The polymeric filter showed a $E_{1/1}$-value of 840 in $CHCl_3$ at 309 nm, which corresponds to the theoretical chromophore content of 64% (w/w). The solubility in Tegosoft TN ($C_{12}$-$C_{15}$ alkylbenzoate) was determined to be at least 24% (w/w).

EXAMPLE 2

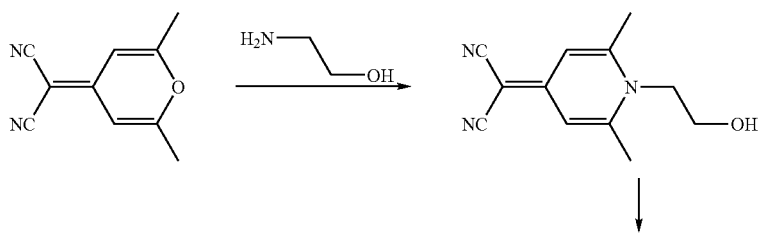

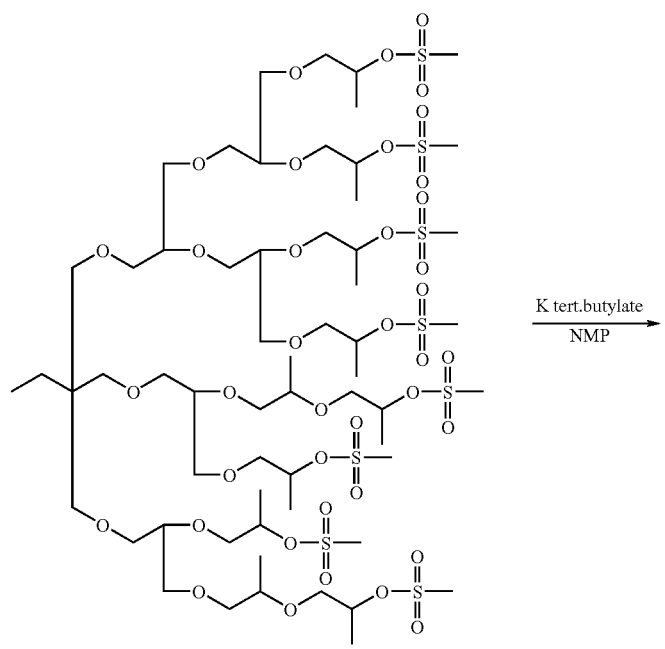

-continued

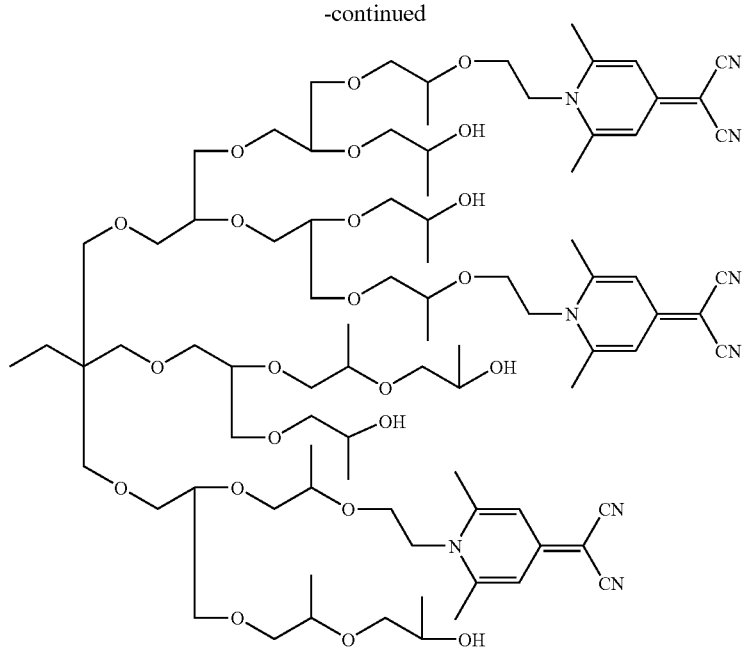

a) 4-Dicyanomethylene-2,6-dimethyl-1,4-dihydropyridine-N-ethane-2-ol

A 350 ml three necked reaction flask, equipped with a thermometer, a reflux condenser and an oil bath with a magnetic stirrer was charged with 4-dicyanomethylene-4H-pyran (25.8 g, 150 mmol, prepared according Helv. Chim. Acta 1962, 1908-1917) in ethanolamine (100 mL, Fluka) and heated to 80° C. for 30 Min. under Ar atmosphere. Shortly after the start, an exothermic reaction is observed. After cooling, the mixture is diluted with n-Butanol (100 mL) and filtered off. The filter residue was washed consecutively with cold water (2×10 mL) and Acetone (2×100 mL). After drying slightly yellowish crystals (17.5 g) were obtained. M.p. 267-268° C. UV (THF) 360 and 372 nm (26'305).

b) Hyperbranched UV-A Filter

Potassium tert. butylate (2.3 g) were added to a solution of 4-Dicyanomethylene-2,6-dimethyl-1,4-dihydropyridine-N-ethane-2-ol (4.3 g, 20 mmol) in NMP (50 mL) and the mixture stirred under Argon at rt. for 10 min. A solution of mesylated poly(glycerol-b-propylene oxide) (4.5 g, 2.3 mmol) in NMP (20 mL) was added dropwise and the reaction mixture stirred at rt. for 6 days. 10% aq. NaHCO$_3$ solution (150 ml) were added and extracted with ethyl acetate (3×100 mL), a precipitate was separated by filtration. The combined organic phases were washed with water (3×100 mL) and saturated NaCl solution (100 mL) and concentrated to yield 4 g of a red oil. This product was chromatographed in Ethylacetate/Ethanol=19:1 and the fractions were analyzed by GPC. A middle fraction of 390 mg showed an UV absorption in THF of E=477 at 370 nm. This corresponds to an average loading of 3.2 chromophores per molecule.

EXAMPLE 3

Preparation of a Brij Formulation Containing 5% (w/w) of Chromophore II as a O/W Sunscreen The hyperbranched chromophore II (5.0 g, corresponding to 5% (w/w) UV-filter/sunscreen) was dissolved in Tegosoft TN at 80° C. and added to a mixture of Brij 72 (INCI: Steareth-2) (2.0 g), Brij 721 (INCI: Steareth-21) (2.0 g), Lanette O (cetearyl alcohol) (2.0 g), Estol GMM 3650 (glyceryl monomyristate) (2.0 g), BHT (butylhydroxytoluene) (0.05 g) and Phenonip (phenoxyethanol and methyl-, ethyl-, propyl-, butylparaben) (0.8 g). The mixture was shortly heated to 80° C. in order to melt solid emulsifiers. To the still warm mixture (70-80° C.) a preheated solution (~80° C.) of glycerin (4.0 g) and EDTA BD (0.1 g) in water (62.95 g) and subsequently 10% aqueous KOH (0.1 g) as well as Sepigel 305 (polyacrylamide and C$_{13}$-C$_{14}$ isoparaffin and Laureth-7) (1.0 g) were added slowly under continuous stirring. The resulting emulsion was stirred until a temperature of about 40° C. was reached, homogenized with 24,000 rpm using a ULTRA-TURRAX®, and finally stirred for an additional hour. Determination of the photostability of the novel polymeric chromophore II was performed according to G. Berset et al. (International Journal of Cosmetic Science 1996, 18(3), 167-177) applying instead of a liquid film the prepared sunscreen. Thereby 96% of the chromophore II could have been recovered. In vitro SPF measurements were performed in comparison to a sunscreen containing 5% Parsol® MCX (2-ethylhexyl 4-methoxycinnamate) after application of 1.4 mg sunscreen per cm$^2$ on PMMA plates (Helioscience, Marseille, FR) using the SPF-290S Analyzer System (Optometrics LLC, Chicago, US). Each in vitro SPF was determined in triplicate to give for chromophore II and Parsol® MCX an average of 6.6 (II) and 6.8, respectively.

EXAMPLE 4

Preparation of a Polymeric UV-Filter by Attaching 4-(dimethylamino)benzoyl chloride to Hybrane® D2000

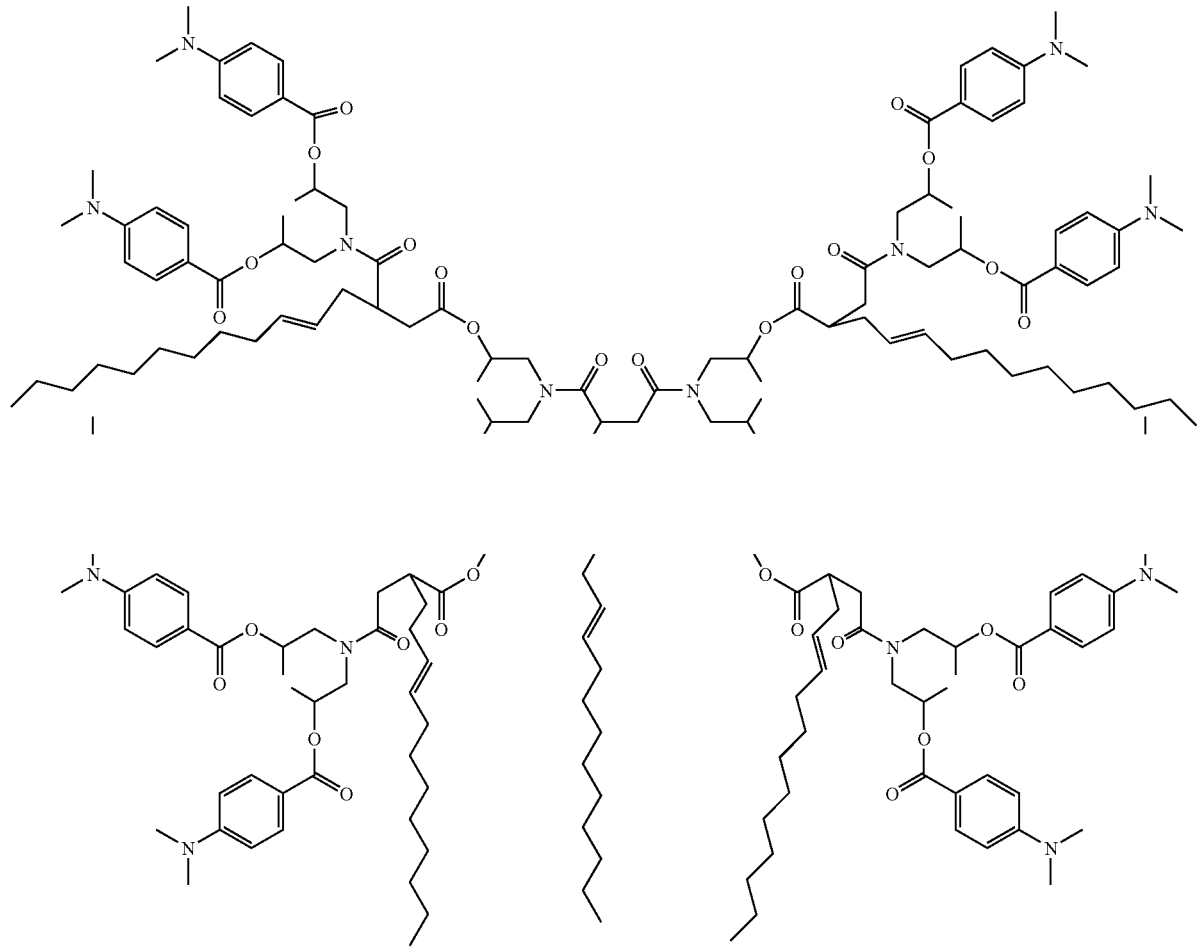

Hybrane® D2000 (WO 99/16810) was supplied from DSM Hybrane (Geleen, The Netherlands) with a Mn of about 2000 g/mol as determined by GPC.

Triethylamine (4.0 mL, 29.0 mmol) and DMAP (50 mg) were added to a solution of Hybrane® D2000 (5.0 g, 2.5 mmol, 20.0 mmol OH) in DCM (75 mL) under Argon at 0° C. Subsequently a solution of 4-(dimethylamino)benzoyl chloride (4.5 g, 24 mmol) in DCM (25 mL) was added dropwise keeping the temperature below 5° C. The reaction mixture was stirred at room temperature for 48 h. Excess acid chloride was hydrolyzed by addition of water (100 mL) and stirring for another 12 h at room temperature. The phases were separated and the aqueous phase was extracted with DCM (2×50 mL). The combined organic phases were washed with saturated bicarbonate solution (150 mL) and 2 N HCl (150 mL). Each organic phase was re-extracted with DCM (50 mL). The combined organic extracts were dried over sodium sulfate, filtered and evaporated under vacuo. The oily residue was purified by column chromatography (ethyl acetate/n-hexane, 1:2 ⇒ ethyl acetate) on silica to yield 6.46 g chromophore III. Total conversion of hydroxy groups was confirmed by the absence of OH oscillation signal at 3500-3600 $cm^{-1}$ using FT-IR analysis. The amount of attached chromophore was determined using $^1H$ NMR, comparing the integration of the signals of the aromatic protons at 6.59 and 7.85 ppm to the $CH_3$ of the aliphatic chain at 0.86 ppm, to give an average of about 8 chromophores/polymer. The polymeric filter showed a $E_{1/1}$-value of 440 in $CHCl_3$ at 311 nm, which corresponds to the theoretical chromophore content of 45% (w/w). The solubility in Tegosoft TN was determined to be at least 22% (w/w).

The same product was obtained, when a mixture of Dodecenyl succinic anhydride (26.6 g, 100 mmol), Diisopropanolamine (17.2 g, 129 mmol) and 4-(N,N-Dimethylamino)-benzoic acid (25.2 g, 153 mmol) was heated under mechanical stirring in an inert atmosphere to 70° C. and then with vacuum to 170° C. during 6 hours. The reaction water was distilled off to get this Polymer as a residue.

EXAMPLE 5

Preparation of a Brij Formulation Containing 5% (w/w) of Chromophore III as a O/W Sunscreen The sunscreen was assembled exactly in the same way as in Example 3 by using the hyperbranched polymeric chromophore III (5.0 g, corresponding to 5% (w/w) UV-filter/sunscreen) instead of chromophore II. The in vitro SPF was determined as described in Example 3 to give 5.8.

EXAMPLE 6

Preparation of a Polymeric Broadband UV-Filter by Attaching 4-(dimethylamino)benzoic Acid and 2-(4-Diethylamino-2-hydroxybenzoyl)benzoic Acid to Hybrane® D2000

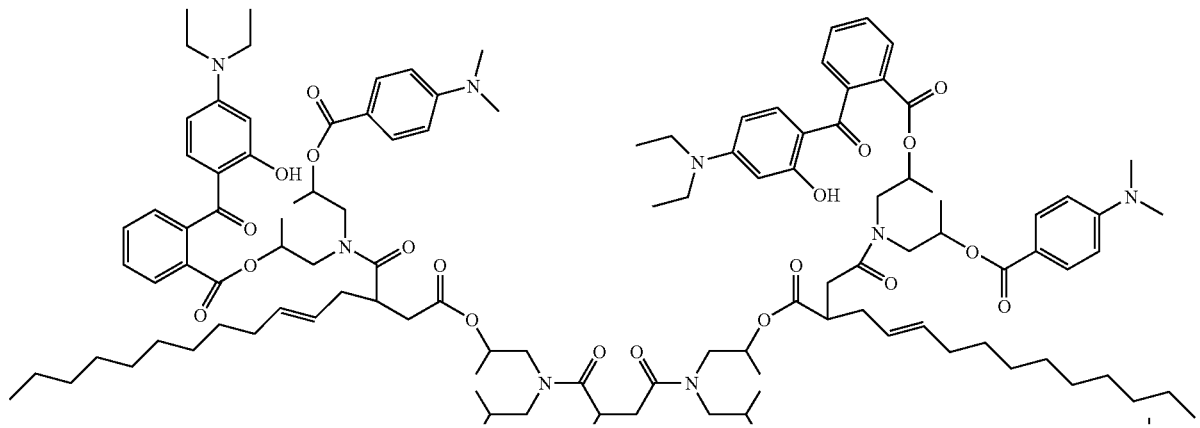

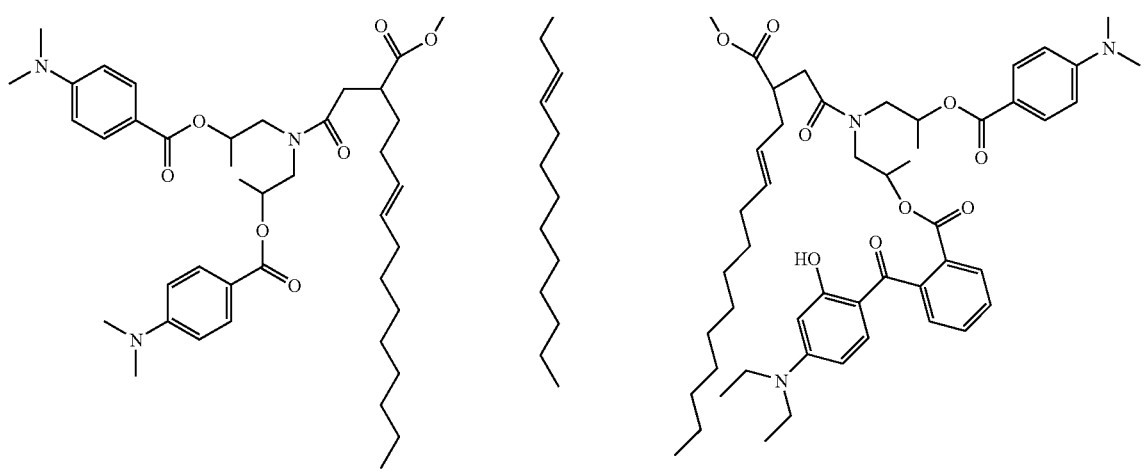

Hybrane® D2000 (WO 99/16810) was supplied from DSM Hybrane (Geleen, The Netherlands) with a Mn of about 2000 g/mol as determined by GPC. 2 g (=8 meq. of OH groups) of Hybrane D2000, 0.63 g (2 mmol) of 2-(4-Diethylamino-2-hydroxybenzoyl)benzoic acid (TCI Europe nv; CAS 5809-23-4) and 1.24 g (6 mmol) of N,N'-Dicyclohexylcarbodiimide (DCC) is dissolved in 20 ml of DMF at room temperature. The reaction is traced by HPLC. After one hour, 0.54 g (2 mmol) of 4-(dimethylamino)benzoic acid, dissolved in 5 ml of DMF is slowly added and stirring is continued with heating to 65° C. for 18 hours. The solvent is evaporated at the Rotavap using high vacuum and the residue is dissolved in Ethylacetate/Hexane=1:1, washed twice with water, dried over Sodium sulfate, filtered and concentrated to form a honey like material. This is chromatographed over Silica starting with Ethylacetate/Hexane=1:2 and ending with pure Ethylacetate. 0.95 g of a brown, honey like product is obtained.

EXAMPLE 7

Preparation of a Polymeric Broadband UV-Filter by Attaching 4-(dimethylamino)benzoic Acid Chloride to the UV-A Filter Obtained in Example 2

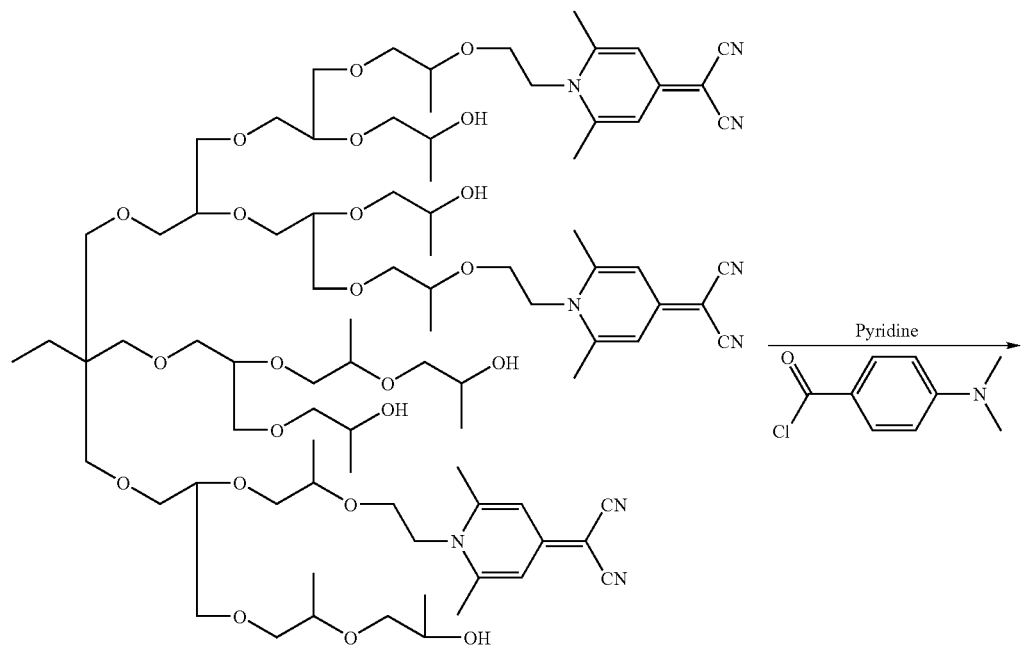
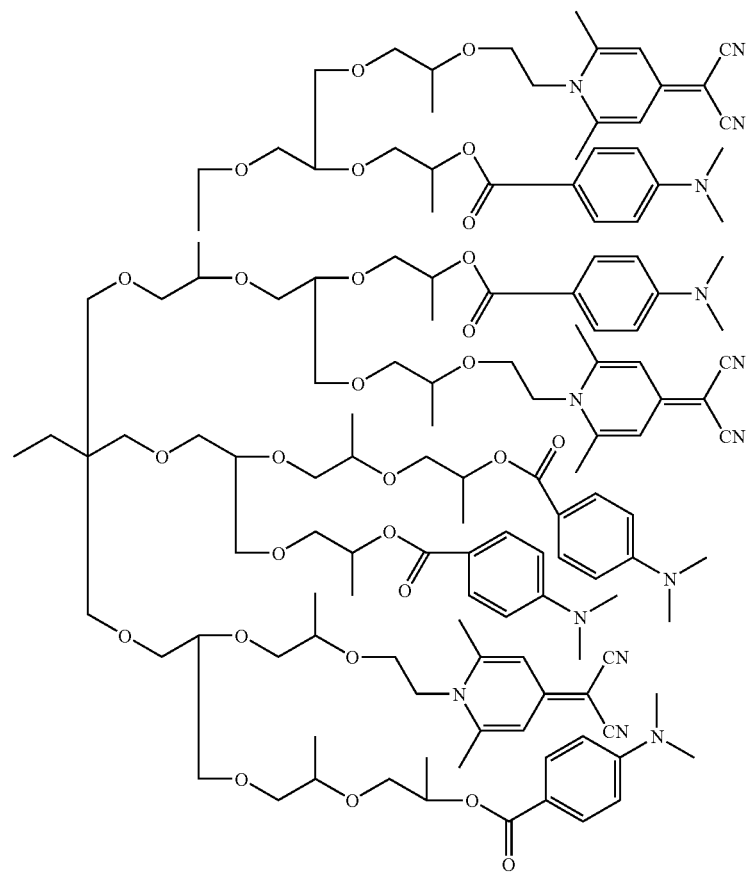

170 mg (~0.1 mmol) of the hyperbranched UV-A filter of example 2b and two drops of DMAP are dissolved in 5 ml of dry Pyridine and 150 mg (ca. 0.8 mmol) of 4-(dimethylamino) benzoyl chloride are added to this solution. This mixture is stirred under Argon at 0° C. for two hours and then heated to 45° C. for another 18 hours. Two drops of distilled water is added, and the stirring is continued for further 60 minutes. The crude mixture is diluted with 50 ml of Ethylacetate and washed twice with 50 ml of sat. aq. Na$_2$CO$_3$ solution followed by 2×50 ml of 1 n HCl and finally with 50 ml of aq. NaCl solution. The combined organic phase is dried over Na$_2$SO$_4$ and concentrated at the Rotavap. The brown, honey like residue is chromatographed over Silica using EtOAc/EtOH=18:2 as eluent to obtain after high vacuum drying a dark yellow foam of the desired product.

EXAMPLE 8

Preparation of a Polymeric Lipophilic and Easily Soluble UV-A Filter by Attaching 2-Ethyl Hexoic Acid Chloride to the Product of Example 2

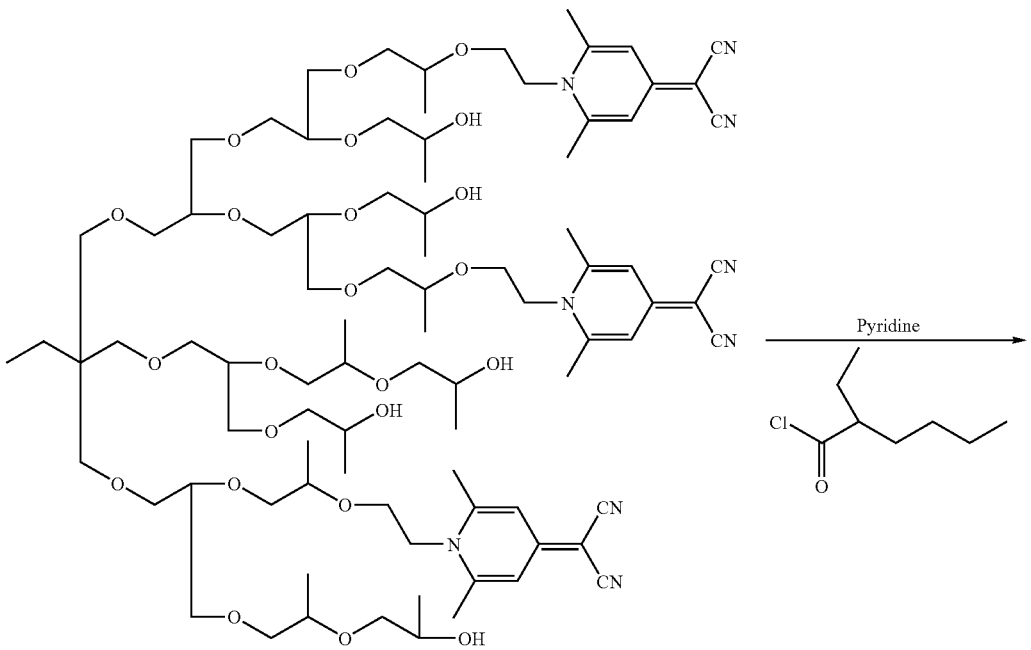

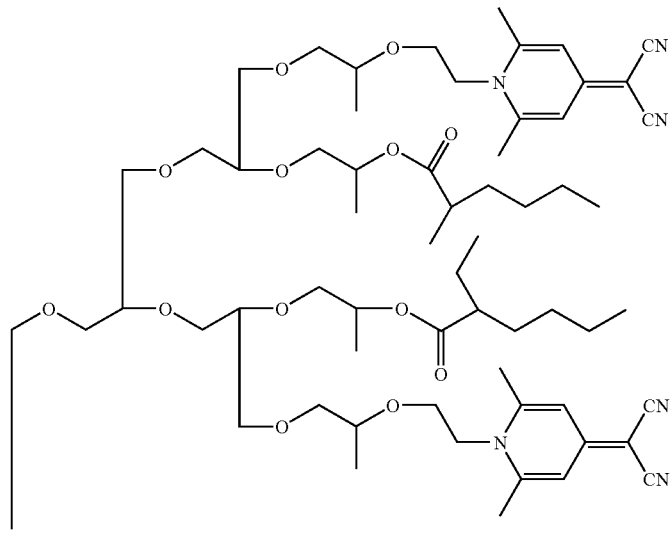

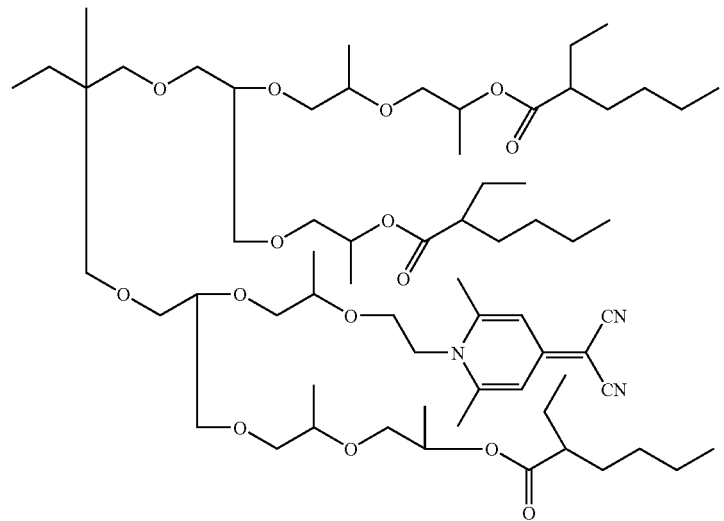

The same procedure as in example 7 is carried out except that the 4-(dimethylamino) benzoyl chloride is replaced by 2-Ethyl hexoic acid chloride. The product is chromatographed over Silica using Hexane/EtOAc=1:1 as eluent to obtain after high vacuum drying a redish oil of the desired product.

EXAMPLE 9

Preparation of a Polymeric, Lipophilic UV-Filter by Attaching 4-(1,3-benzoxazol-2-yl)-phenol to an Activated Poly(glycerol-b-propylene Oxide) Followed by Ethoxylation

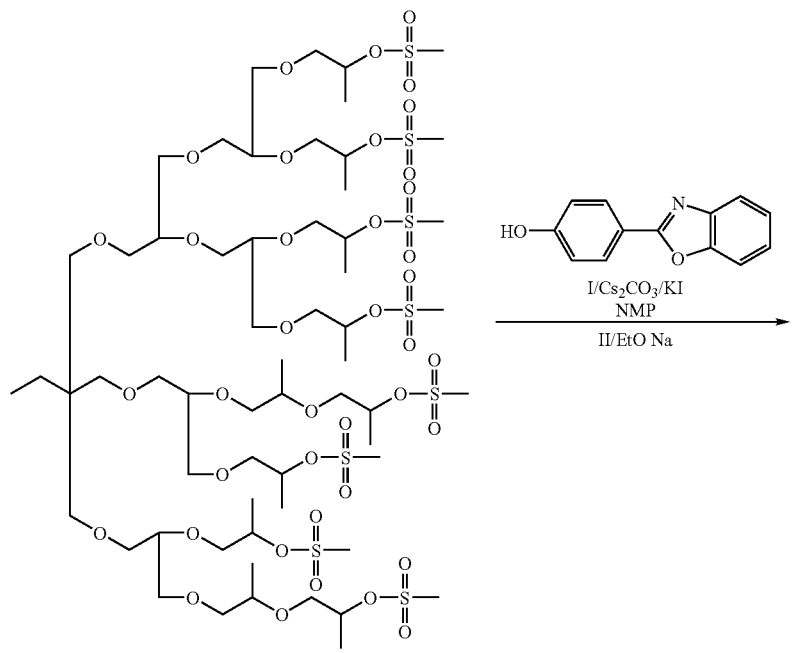

-continued

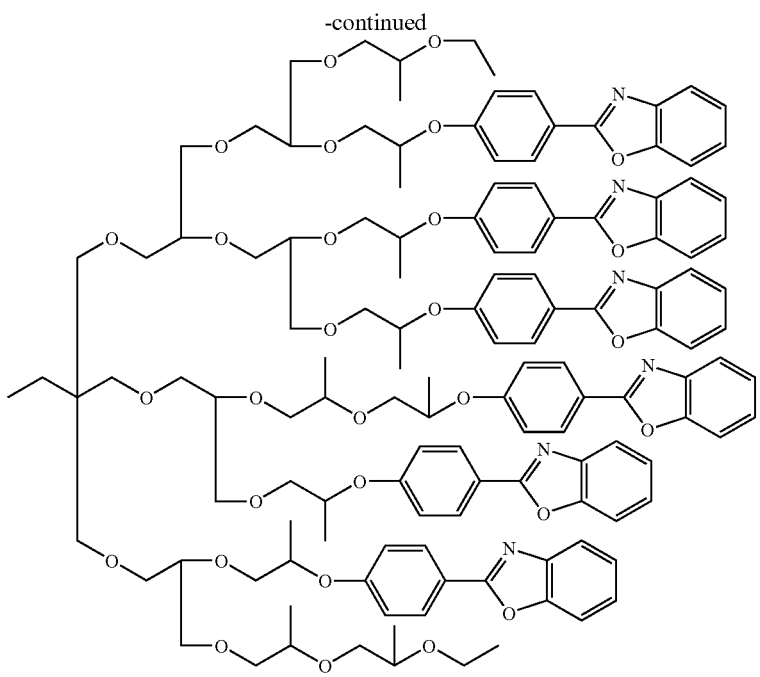

The same reaction is carried out as in example 1b, but only 5.5 g (26 mmol) of 4-(1,3-benzoxazol-2-yl)-phenol is applied instead of 8.9 g. The reaction mixture is heated for five hours to 80° C., cooled to room temperature and a solution of 2.7 g (40 mmol) of dry Sodium ethylate in 10 ml NMP is slowly added. The reaction is again heated to 80° C. for two hours and then worked up and chromatographed as described before to yield 3.3 g of the desired product.

The invention claimed is:

1. A cosmetic composition comprising a conjugate comprising a hyperbranched polymer covalently bonded to at least three UV absorbing chromophores having an UV absorption maximum $\lambda_{max} \geq 270$ nm selected from the group consisting of the moieties represented by general formulae:

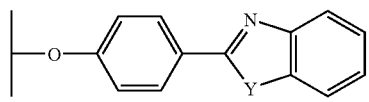
(V-A)

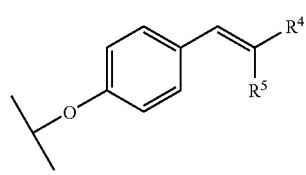
(V-B)

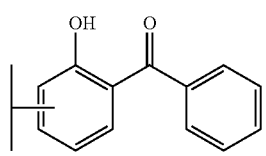
(V-C)

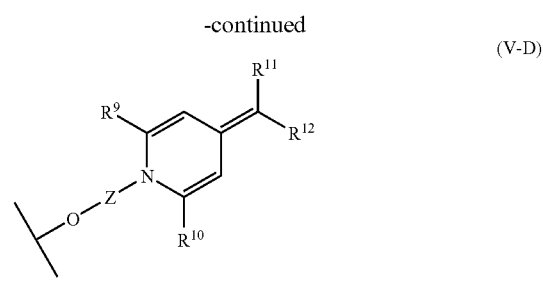
(V-D)

(V-E)
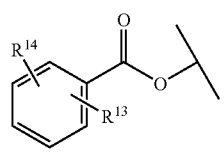

(V-F)
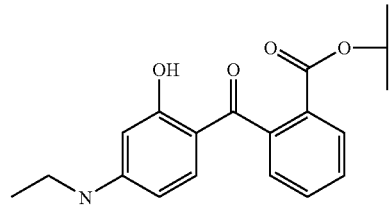

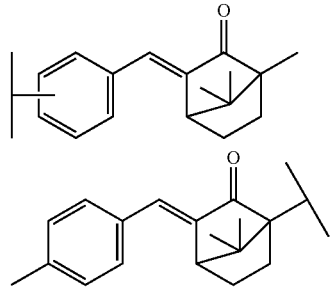

-continued

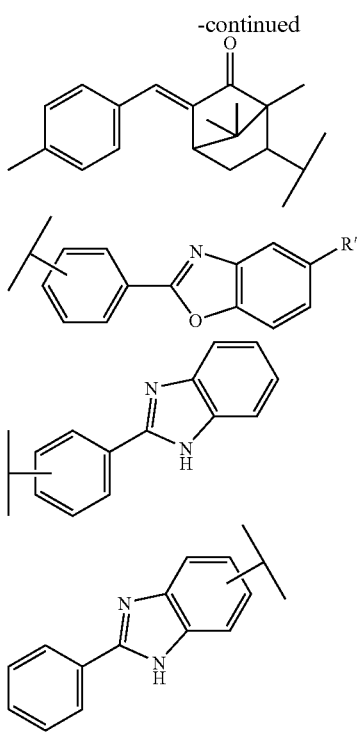

wherein

Y is O or NR$^3$ wherein R$^3$ is H, C$_1$-C$_6$-alkyl or C$_2$-C$_6$-alkenyl;

R$^4$ and R$^5$ are independently H, C$_1$-C$_6$-alkyl, C$_2$-C$_6$-alkenyl, CO$_2$H, CO$_2$—C$_1$-C$_6$-alkyl, or R$^4$ and R$^5$ together with the carbon atom to which they are attached form a 6-camphenyl ring;

R$^9$ and R$^{10}$ are independently H or C$_1$-C$_6$-alkyl;

R$^{11}$ and R$^{12}$ are independently H, C$_1$-C$_6$-alkyl, NO$_2$, CO$_2$—C$_1$-C$_6$-alkyl or CN;

Z is C$_1$-C$_6$-alkylene, optionally interrupted by 1 to 3 oxygen atoms;

R$^{13}$ and R$^{14}$ are independently H, OR$^{15}$, NR$^{16}$R$^{17}$ or C$_1$-C$_6$-alkyl; and R$^{15}$, R$^{16}$ and R$^{17}$ are independently selected from H and C$_1$-C$_6$-alkyl; and wherein R' is H, OH, straight or branched chain C$_1$-C$_{20}$-alkyl, C$_1$-C$_{20}$-alkoxy or C$_2$-C$_{20}$-alkenyl;

and wherein in the above definition the symbol "—" denotes the linkage to the hyperbranched polymer;

or a moiety of benzophenone-3, benzophenone-4, 2,2',4,4'-tetrahydroxy-benzophenone and 2,2'-dihydroxy-4,4' dimethoxybenzophenone;

and a cosmetically acceptable carrier, and wherein the hyperbranched polymer is the polycondensation or polyaddition reaction product of building blocks AB$_2$, which building block AB$_2$ is glycidol.

2. The composition according to claim 1, wherein the hyperbranched polymer exhibits an average degree of branching ≧25%.

3. The composition according to claim 1, wherein the hyperbranched polymer has an average molecular weight M$_W$ within the range of from 500 to 50,000 g mol$^{-1}$.

4. The composition according to claim 1, wherein the hyperbranched polymer comprises an average number of 2 to 600 dendritic building blocks.

5. The composition according to claim 1, wherein the hyperbranched polymer comprises a structure represented by general formula (I)

$$\{[Q](Y^1)_g\}(LX)_p(Y^2)_h \qquad (I),$$

wherein

Y$^1$ and Y$^2$ independently represent UV absorbing chromophores;

$\{[Q](Y^1)_g\}$ represents the hyperbranched polymer covalently bonded to g UV absorbing chromophores Y$^1$;

(LX)$_p$ represents p linker units LX, wherein independently the distal end of each linker unit LX bears a functional group X either being covalently bonded to an UV absorbing chromophore Y$^2$, or covalently bonded to a capping group, or in its free reactive form, and wherein the proximal end of each linker unit LX is covalently bonded to the hyperbranched polymer; and wherein index g is an integer, wherein 0≦g≦100;

index h is an integer, wherein 0≦h≦p; and index p is an integer, wherein 0≦p≦100;

with the proviso that g+h≧3.

6. A cosmetic composition comprising a conjugate comprising a hyperbranched polymer covalently bonded to at least three UV absorbing chromophores having an UV absorption maximum λ$_{max}$≧270 nm selected from the group consisting of the moieties represented by general formulae:

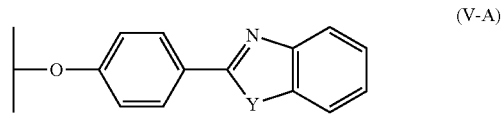
(V-A)

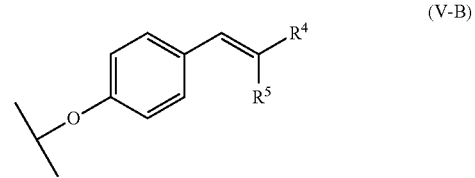
(V-B)

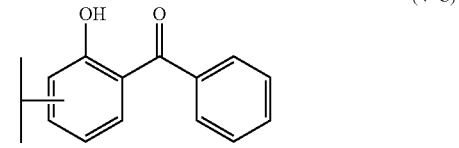
(V-C)

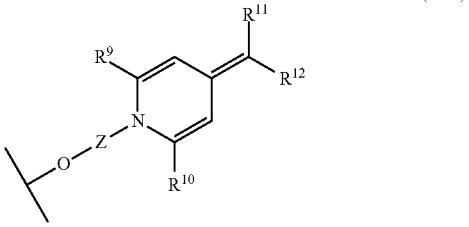
(V-D)

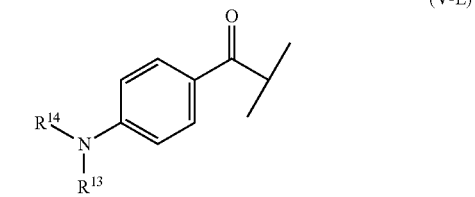
(V-E)

-continued

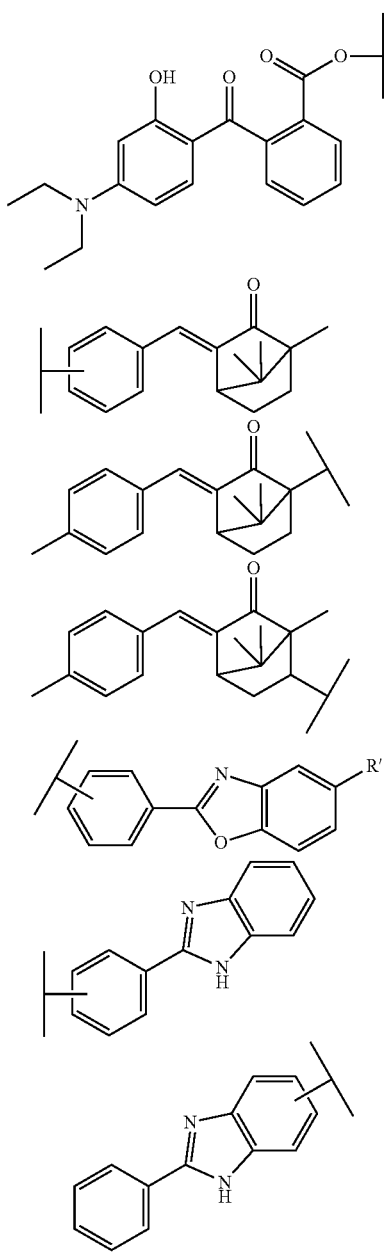

wherein
Y is O or NR$^3$ wherein R$^3$ is H, C$_1$-C$_6$-alkyl or C$_2$-C$_6$-alkenyl;
R$^4$ and R$^5$ are independently H, C$_1$-C$_6$-alkyl, C$_2$-C$_6$-alkenyl, CO$_2$H, CO$_2$-C$_1$-C$_6$-alkyl, or R$^4$ and R$^5$ together with the carbon atom to which they are attached form 6-camphenyl ring;
R$^9$ and R$^{10}$ are independently H or C$_1$-C$_6$alkyl;
R$^{11}$ and R$^{12}$ are independently H, C$_1$-C$_{6\text{-}alkyl}$, NO$_2$, CO$_2$-C$_1$-C$_6$-alkyl or CN;
Z is C$_1$-C$_6$-alkylene, optionally interrupted by 1 to 3 oxygen atoms;
R$^{13}$ and R$^{14}$ are independently H, OR$^{15}$, NR$^{16}$R$^{17}$ or C$_1$-C$_6$-alkyl; and
R$^{15}$, R$^{16}$ and R$^{17}$ are independently selected from H and C$_1$-C$_6$-alkyl; and wherein R' is H, OH, straight or branched chain C$_1$-C$_{20}$-alkyl, C$_1$-C$_{20}$-alkoxy or C$_2$-C$_{20}$-alkenyl;
and wherein in the above definition the sysmbol "⊣" denotes the linkage to the hyperbranched polymer;
or a moiety of benzophenone-3, benzophenone-4, 2,2',4,4'-tetrahydroxy-benzophenone and 2,2'-dihydroxy-4,4'dimethoxybenzophenone;
and a cosmetically acceptable carrier, wherein the hyperbrqanched polymer comprises a structure represented by general formula (II)

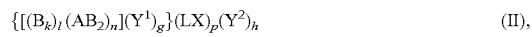

wherein
Y$^1$ and Y$^2$ independently represent UV absorbing chromophores;
(LX)$_p$ represents p linker units LX, wherein independently the distal end of each linker unit LX bears a functional group X either being covalently bonded to an UV absorbing chromophore Y$^2$, or covalently bonded to a capping group, or in its free reactive form,
and wherein the proximal end of each linker unit LX is covalently bonded to the hyperbranched polymer; and
B$_k$ represents a starter unit bearing k functional groups B, wherein independently each functional group B is
covalently bonded to a functional group A of a building block AB$_2$; or
covalently bonded to the proximal end of a linker unit LX, or
covalently bonded to an UV absorbing chromophore Y$^1$, or
covalently bonded to a capping group, or
in its free reactive form;
(AB$_2$)$_n$ represents n building blocks AB$_2$, which building block is glycidol, each bearing a functional group A which is the electrophillic carbon atom of the oxirane and 2 independent functional groups B which are represented by the alcoholate of deprotonated glycidol as well as the alcoholate deliberated upon ring opening, wherein independently each functional group A is
covalently bonded to a functional group B
of a further building block AB$_2$, which building block is glycidol, or
of the starter unit B$_k$, or
covalently bonded to a capping group, or
in its free reactive form,
and wherein independently each functional group B is
covalently bonded to a functional group A of a further building block AB$_2$, which building block is glycidol, or
covalently bonded to the proximal end of a linker unit LX, or
covalently bonded to an UV absorbing chromophore Y$^1$, or
covalently bonded to a capping group, or
in its free reactive form;
wherein
index g is an integer, wherein 0≦g≦100;
index h is an integer, wherein 0≦h≦p, with the proviso that g+h≧3;
index k is an integer of from 1 to 6;
index l is 0 or 1;
index n is an integer of from 3 to 100; and
index p is an integer wherein 0≦p≦100.
7. The composition according to claim 6, wherein in the hyperbranched polymer index l is 1, the starting unit B$_k$ is trimethylolpropane and the building block AB$_2$ is glycidol.

8. The composition according to claim 5, wherein the hyperbranched polymer comprises a structure represented by general formula (III)

$$\{[(B_k)_l(AB_2)_n(C_g)_r](Y^1)_g\}(LX)_p(Y^2)_h \qquad (III),$$

wherein
Y$^1$ and Y$^2$ are as defined previously;
LX is as defined previously;
$B_k$ represents a starter unit bearing k functional groups B, wherein independently each functional group B is
   covalently bonded to a functional group C
      of a monomer C$_2$ or
      of a building block C$_q$ or
   covalently bonded to the proximal end of a linker unit LX, or
   covalently bonded to an UV absorbing chromophore Y$^1$, or
   covalently bonded to a capping group, or
   in its free reactive form;
$(AB_2)_n$ represents n building blocks AB$_2$, each bearing a functional group A and 2 independent functional groups B, wherein independently each functional group A is
   covalently bonded to a functional group C
      of a monomer C$_2$ or
      of a building block C$_q$, or
   covalently bonded to the proximal end of a linker unit LX, or
   covalently bonded to an UV absorbing chromophore Y$^1$, or
   covalently bonded to a capping group, or
   in its free reactive form;
and wherein independently each functional group B is
   covalently bonded to a functional group C
      of a monomer C$_2$ or
      of a building block C$_q$, or
   covalently bonded to the proximal end of a linker unit LX, or
   covalently bonded to an UV absorbing chromophore Y$^1$, or
   covalently bonded to a capping group, or
   in its free reactive form;
$(C_q)_r$ represents
   when index q=2: r monomers C$_2$ or
   when index q>2: r building blocks C$_q$
each bearing q functional groups C, wherein independently each functional group C is
   covalently bonded to a functional group A of a building block AB$_2$, or
   covalently bonded to a functional group B
      of a building block AB$_2$, or
      of the starter unit $B_k$, or
   covalently bonded to the proximal end of a linker unit LX, or
   covalently bonded to an UV absorbing chromophore Y$^1$, or
   covalently bonded to a capping group, or
   in its free reactive form;
wherein
index g is as defined previously;
index h is as defined previously;
index k is an integer of from 1 to 6;
index l is 0 or 1;
index n is an integer of from 3 to 100;
index p is an integer wherein $0 \leq p \leq 100$;
index q is an integer of from 2 to 4; and
index r is an integer wherein $1 \leq r \leq 2n/q$.

9. The composition according to claim 5 or 6, wherein the linker unit LX in the hyperbranched polymer comprises polyethyleneoxide or polypropyleneoxide.

10. The composition according to claim 5 or 6, wherein the hyperbranched polymer comprises 1 to 20 capping groups.

11. The composition according to claim 10, wherein the capping group is a straight or branched chain ether or ester group with 1 to 20 carbon atoms.

* * * * *